US010450612B2

(12) United States Patent
Breen

(10) Patent No.: US 10,450,612 B2
(45) Date of Patent: Oct. 22, 2019

(54) CHROMOSOMAL ASSESSMENT TO DIAGNOSE UROGENITAL MALIGNANCY IN DOGS

(71) Applicant: North Carolina State University, Raleigh, NC (US)

(72) Inventor: Matthew Breen, Apex, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 15/037,438

(22) PCT Filed: Nov. 14, 2014

(86) PCT No.: PCT/US2014/065773
§ 371 (c)(1),
(2) Date: May 18, 2016

(87) PCT Pub. No.: WO2015/073870
PCT Pub. Date: May 21, 2015

(65) Prior Publication Data
US 2016/0289767 A1 Oct. 6, 2016

Related U.S. Application Data

(60) Provisional application No. 61/904,659, filed on Nov. 15, 2013.

(51) Int. Cl.
*C12Q 1/68* (2018.01)
*C07H 21/04* (2006.01)
*C12Q 1/6886* (2018.01)
*C12Q 1/6827* (2018.01)

(52) U.S. Cl.
CPC ......... *C12Q 1/6886* (2013.01); *C12Q 1/6827* (2013.01); *C12Q 2537/16* (2013.01); *C12Q 2600/112* (2013.01); *C12Q 2600/124* (2013.01); *C12Q 2600/158* (2013.01)

(58) Field of Classification Search
None
See application file for complete search history.

(56) References Cited

U.S. PATENT DOCUMENTS

| | | |
|---|---|---|
| 6,251,601 B1 | 6/2001 | Bao et al. |
| 6,905,823 B2 | 6/2005 | Kallioniemi et al. |
| 7,930,104 B2 | 4/2011 | Baker et al. |
| 7,960,110 B2 | 6/2011 | Bastian et al. |
| 9,090,945 B2 | 7/2015 | Breen |
| 9,290,814 B2 | 3/2016 | Giafis et al. |
| 2007/0275403 A1 | 11/2007 | Morrison et al. |
| 2009/0155805 A1 | 6/2009 | Zhang et al. |
| 2009/0299640 A1 | 12/2009 | Ellis et al. |
| 2009/0324596 A1 | 12/2009 | Kang et al. |
| 2013/0011834 A1 | 1/2013 | Breen |
| 2013/0171637 A1 | 7/2013 | Giafis et al. |
| 2013/0210014 A1 | 8/2013 | Sharman |
| 2017/0211150 A1 | 7/2017 | Breen |

FOREIGN PATENT DOCUMENTS

| | | |
|---|---|---|
| EP | 2 513 340 B1 | 6/2016 |
| WO | WO2002/077197 | 10/2002 |
| WO | 02/100246 A2 | 12/2002 |
| WO | 2009051842 A2 | 4/2009 |
| WO | WO2012/078053 | 6/2012 |
| WO | 2012135125 A1 | 10/2012 |
| WO | WO 2017/210115 | 12/2017 |

OTHER PUBLICATIONS

Thomas et al. (Am. Genetic Association, vol. 98,No. 5, pp. 474-484, 2007). (Year: 2007).*
Bowman et al. (Molecular Evaluation of Canine Urothelial Carcinoma and the Cell line Model, NCSU CVM Annual Research Forum Award of Excellence for Poster presentation, Feb. 2013). (Year: 2013).*
Thomas, Chromosome Res,vol. 22, No. 3, pp. 305-319, 2017 (Year: 2017).*
Thomas et al. (Chromosome Research, vol. 10, Apr. 1, 2009 (Year: 2009).*
Lin et al. (Veterinary Immunology and Immunopathology, vol. 127, pp. 114-124, 2009) (Year: 2009).*
Extended European Search Report issued in counterpart European Application No. 14861374.8 dated May 29, 2017 (eleven (11) pages).
Lin Tzu-Yin et al: "Targeting canine bladder transitional cell carcinoma with a human bladder cancer-specific ligand", Molecular Cancer, Biomed Central, London, GB, vol. 10, No. 1, Jan. 27, 2011 (Jan. 27, 2011), p. 9, XP02108845 9 , ISSN: 1476-4598, DOI: 10.1186/1476-4598-10-9.
Marin-Aguilera Mercedes et al: "Utility of Fluorescence in Situ Hybridization as a Non-invasive Technique in the Diagnosis of Upper Urinary Tract Urothelial Carcinoma", European Urology, vol. 51, No. 2, Aug. 22, 2006 (Aug. 22, 2006), pp. 409-415, XP029850986, ISSN: 0302-2838, DOI: 10.1016/J.EURURO.2006.08.045.
Magdy Sayed Aly et al: "Chromosomal aberrations in early-stage bilharzial bladder cancer", Cancer Genetics and Cytogenetics., vol. 132, No. 1, Jan. 1, 2002 (Jan. 1, 2002), pp. 41-45, XP055372968, us ISSN: 0165-4608, DOI: 10 . 1016/80165-4608(01)00527-1.
Maria I. Stamouli et al: "Detection of genetic alterations in primary bladder carcinoma with dual-color and multiplex fluorescence in situ hybridization", Cancer Genetics and Cytogenetics., vol. 149, No. 2, Mar. 1, 2004 (Mar. 1, 2004), pp. 107-113, XP055372972, us ISSN: 0165-4608, DOI: 10 . 1016/80165-4608(03)00303-0.
R. Thomas et al: "A Cytogenetically Characterized, Genome-Anchored 10-M b BAC Set and CGH Array for the Domestic Dog", Journal of Heredity., vol. 98, No. 5, Jul. 23, 2007 (Jul. 23, 2007), pp. 474-484, XP055343142, GB ISSN: 0022-1503, DOI: 10.1093/jhered/esm053.

(Continued)

*Primary Examiner* — Jeanine A Goldberg
(74) *Attorney, Agent, or Firm* — Jenkin, Wilson, Taylor & Hunt, P.A.

(57) ABSTRACT

This invention is directed to a method of diagnosing bladder cancer in dogs.

17 Claims, 6 Drawing Sheets

Specification includes a Sequence Listing.

(56) References Cited

OTHER PUBLICATIONS

Breen et al. "Chromosome-Specific Single-Locus FISH Probes Allow Anchorage of an 1800-Marker Integrated Radiation-Hybrid/Linkage Map of the Domestic Dog Genome to All Chromosomes", Genome Research, 11: 1784-1795 (2001).
Breen, Matthew, et al. "An integrated 4249 marker FISH/RH map of the canine genome." BMC genomics 5(1): 65 (2004).
International Preliminary Report on Patentability for related PCT Application No. PCT/US2014/065773 dated May 17, 2016.
International search report and the written opinion of the international searching authority for a related PCT Application No. PCT/US2014/065773 dated May 21, 2015.
Mutsaers, Anthony J., et al. "Canine transitional cell carcinoma." Journal of veterinary internal medicine 17(2): 136-144 (2003).
Seiser, E. L., et al. "Reading between the lines: molecular characterization of five widely used canine lymphoid tumour cell lines." Veterinary and comparative oncology 11(1): 30-50 (2013).
Sotirakopolous et al: "Evaluation of Microsatellite Instability in Urine for the Diagnosis of Transitional Cell Carcinoma of the Lower Urinary Tract in Dogs", J Vet Med, 24: 1445-1451 (2010).
Thomas et al: "A Cytogenetically Characterized, Genome-Anchored 10-Mb BAC Set and CGH Array for the Domestic Dog", Journal of Heredity, 98(5): 474-484 (2007).
Thomas, R., et al. "A genome assembly-integrated dog 1 Mb BAC microarray: a cytogenetic resource for canine ancer studies and comparative genomic analysis." Cytogenetic and genome research 122(2): 110-121 (2008).
Thomas, Rachael, et al. "Refining tumor-associated aneuploidy through 'genomic recoding' of recurrent DNA copy number aberrations in 150 canine non-Hodgkin lymphomas." Leukemia & lymphoma 52(7): 1321-1335 (2011).
UROVYSION Bladder Cancer Kit; <http://www.abbottmolecular.com> Accessed Nov. 11, 2013.
UROVYSION Bladder Cancer Kit; Package Insert; Abbott Laboratories, 2006.
Bowman, Susan et al; "Molecular Evaluation of Canine Urothelial Carcinoma and the Cell Line Model," Department of Molecular Biomedical Sciences, North Carolina State University College of Veterinary Medicine, Raleigh, NC, dated Nov. 17, 2013 (four (4) pages).
Al Mulla et al., "Genetic profiling of stage I and II colorectal cancer may predict metastatic relapse," Modern Pathology. vol. 19, No. 5 pp. 648-658 (2006).
Angstadt, Andrea Y. et al.; "A genome-wide approach to comparative oncology: high-resolution oligonucleotide aCGH of canine and human osteosarcoma pinpoints shared microaberrations," Cancer Genetics, 2012.
Breen et al., An integrated 4249 marker FISH/RH map of the canine genome. BMC Genomics, 5:65. (2004).
Breen, M., "Evolutionarily conserved cytogenetic changes in hematological malignancies of dogs and humans—man and his best friend share more than companionship," vol. 16, No. 1, pp. 145-154 (Feb. 25, 2008).
Decision to grant a European patent pursuant to Article 97(1) EPC for European Patent Application No. 10861217.7 dated Jun. 2, 2016.
European Search Report corresponding to European Patent Application No. 10861217.7-1403/2513340 dated Jun. 3, 2013.
Hahn et al., "Diagnostic and Prognostic Importance of Chromosomal Aberrations Identified in 61 Dogs with Lymphosarcoma," Veterinary Pathology, vol. 31, No. 5, pp. 528-540 (Sep. 1, 1994).
Hedan et al, (BMC Cancer, vol. 11, pp. 1-14, May 26, 2011), (Year: 2011).
International Preliminary Report dated Feb. 2, 2017 from related International Application No. PCT/US2015/41988.
International Search Report and Written Opinion dated Jul. 2, 2015 from related International Application No. PCT/US2015/025916.

International Search Report and Written Opinion dated Oct. 30, 2015 from related International Application No. PCT/US2015/41988.
International Search Report and Written Opinion issued in PCT Application No. PCT/US2017/034711 dated Sep. 14, 2017 (six (6) pages).
Karlin-Neumann al. (2012). Probing copy number variations using Bio-Rad's QX100™ Droplet Digital™ PCR system. Bio-Rad Bulletin 6277.
Koenig, A.; "Expression and Significance of p53, Rb, p21/waf-1, p16/ink-4a, and PTEN Tumor Suppressors in Canine Melanoma," Vet Pathol. 39: 458-472 (2002).
Letard S. et al. "Gain-of-Function Mutations in the Extracellular Domain of KIT Are Common in Canine Mast Cell Tumors" Molecular Cancer Research. 2008 pp. 1137-1145 (ten (10) pages).
Mochizuki, A. et al. "Detection of Copy Number Imbalance in Canine Urothelial Carcinoma With Droplet Digital Polymerase Chain Reaction" Oncology-Original Article, Veterinary Pathology_ 2016, vol. 53(4) pp. 764-772 (nine (9) pages).
Modiano et al., "Predictive value of p16 or Rb inactivation in a model of naturally occurring canine non-Hodgkin's lymphoma," Leukemia. vol. 21, No. 1 pp. 187-187 (2007).
Muller et al. (2012) Genetic characterization via array based comparative genomic hybridization. Tierarztliche Praxis. 40(1):55-58.
Mullins et al. "Agreement in Breast Cancer Classification between Microarray and Quantitative Reverse Transcription PCR from Fresh-Frozen and Formalin-Fixed, Paraffin-Embedded Tissues" Clin Chem. 53(7): 1273-1279 (2007).
Notice of Allowance corresponding to Japanese Patent Application No. 2016-554527 dated Feb. 5, 2019.
Notification Concerning Transmittal of International Preliminary Report on Patentability (Chapter I of the Patent Cooperation Treaty) corresponding to International Patent Application No. PCT/US2010/060292 dated Aug. 30, 2012.
Notification of Transmittal of the International Search Report and the Written Opinion of the International Searching Authority, or the Declaration corresponding to International Patent Application No. PCT/US2010/060292 dated Apr. 10, 2012.
Office Action corresponding to Canadian Patent Application No. 2,785,999 dated Aug. 16, 2016.
Office Action corresponding to U.S. Appl. No. 13/515,614 dated Jul. 30, 2014.
Office Action corresponding with European Patent Application No. 10861217.7-1403 dated Apr. 25, 2014.
Oral Summons corresponding with European Patent Application No. 10861217.1-1403 dated Jun. 12, 2015.
Ratcliffe et al., "Proteomic identification and profiling of canine lymphoma patients," Veterinary and Comparative Oncology. vol. 7, No. 2 pp. 92-105 (2009).
Roode, Sarah Culvar.; "Molecular Characterization of Canine Leukemia—Comparative Value and Clinical Application," A dissertation submitted to the Graduate Faculty of North Carolina State University in partial fulfillment of the requirements for the degree of Doctor of Philosophy; Raleigh, North Carolina, 2014.
Sailasuta, A. et al. "The Relevance of CD117-Immunocytohchemistry Staining Patterns to Mutational Exon-11 in c-kit Detected by PCR from Fine-Needle Aspirated Canine Mast Cell Tumor Cells" Veterinary Medicine International. vol. 2014, pp. 1-8 (eight (8) pages).
Supplementary material for Thomas R, et al.; "Refining tumor-associated aneuploidy through 'genomic recoding' of recurrent DNA copy number aberrations in 150 canine non-Hodgkine lymphomas," Leukemia & Lymphoma, 2011.
Thomas et al., "A canine-gene microarray for CGH analysis of tumors," Cytogenetic and Genome Research, vol. 102, No. 1-4, pp. 254-260 (2003).
Thomas et al., "Chromosome aberrations in canine multicentric lympomas detected with comparative genomic hybridisation and a panel of single locus probes," British Journal of Cancer. vol. 89, No. 8 pp. 1530-1537 (2003).
Thomas, Rachael et al.; "Construction of a 2-Mb resoulution BAG microarray for CGH analysis of canine tumors," Genome Research, pp. 1832-1837, Dated Feb. 13, 2005, Revised May 4, 2005.

(56) References Cited

OTHER PUBLICATIONS

Office Action corresponding with European Patent Application No. 14861374.8-1118 dated Apr. 4, 2019.
Office Action corresponding to Japanese Patent Application No. 2016-554527 dated Sep. 25, 2018. (Translation).
Winkler et al. (2006) Polysomy 13 in a canine prostate carcinoma underlining its significance in the development of prostate cancer. Cancer Genet. Cytogenet. 169:154-158.

* cited by examiner

CFA 8:7.98-8.13Mb

CFA 13:8.65-8.82Mb

CFA 19:25.12-25.26Mb

CFA 36:23.20-23.27Mb

```
                              SEQUENCE LISTING

<160> NUMBER OF SEQ ID NOS: 16

<210> SEQ ID NO 1
<211> LENGTH: 22
<212> TYPE: DNA
<213> ORGANISM: Canis familiaris

<400> SEQUENCE: 1
ccaggattct gcagagtttg at                                                  22

<210> SEQ ID NO 2
<211> LENGTH: 24
<212> TYPE: DNA
<213> ORGANISM: Canis familiaris

<400> SEQUENCE: 2
aatgcctttg accagtgggt agcc                                                24

<210> SEQ ID NO 3
<211> LENGTH: 22
<212> TYPE: DNA
<213> ORGANISM: Canis familiaris

<400> SEQUENCE: 3
gtggtggagg atttggaaga ag                                                  22

<210> SEQ ID NO 4
<211> LENGTH: 103
<212> TYPE: DNA
<213> ORGANISM: Canis familiaris

<400> SEQUENCE: 4
ccaggattct gcagagtttg atttgttgtt tgaaaatgcc tttgaccagt gggtagccag         60
cacagcctca gaaaaatgca ccttcttcca aatcctccac cac                          103

<210> SEQ ID NO 5
<211> LENGTH: 28
<212> TYPE: DNA
<213> ORGANISM: Canis familiaris

<400> SEQUENCE: 5
aggactatgt gtaaatcagt aagatagg                                            28

<210> SEQ ID NO 6
<211> LENGTH: 27
<212> TYPE: DNA
<213> ORGANISM: Canis familiaris

<400> SEQUENCE: 6
tgaatgaggt tgaggatgaa gcaaggt                                             27

<210> SEQ ID NO 7
<211> LENGTH: 21
<212> TYPE: DNA
<213> ORGANISM: Canis familiaris

<400> SEQUENCE: 7
cccacttcat gaccatatcc c                                                   21
```

```
<210> SEQ ID NO 8
<211> LENGTH: 104
<212> TYPE: DNA
<213> ORGANISM: Canis familiaris

<400> SEQUENCE: 8
aggactatgt gtaaatcagt aagataggcc tgtatagtat gaagaatgga ttgaatgagg      60
ttgaggatga agcaaggtta gttgggatat ggtcatgaag tggg                     104

<210> SEQ ID NO 9
<211> LENGTH: 21
<212> TYPE: DNA
<213> ORGANISM: Canis familiaris

<400> SEQUENCE: 9
ggactgctga acttccttca t                                               21

<210> SEQ ID NO 10
<211> LENGTH: 27
<212> TYPE: DNA
<213> ORGANISM: Canis familiaris

<400> SEQUENCE: 10
aggtccaata ttgcaatgag tgaagca                                         27

<210> SEQ ID NO 11
<211> LENGTH: 20
<212> TYPE: DNA
<213> ORGANISM: Canis familiaris

<400> SEQUENCE: 11
ctgtggcttc ctcatcgttt                                                 20

<210> SEQ ID NO 12
<211> LENGTH: 107
<212> TYPE: DNA
<213> ORGANISM: Canis familiaris

<400> SEQUENCE: 12
ggactgctga acttccttca tttctcagtc atcagcaaac taagagaagt aaactttaag     60
gtccaatatt gcaatgagtg aagcataaaa cgatgaggaa gccacag                  107

<210> SEQ ID NO 13
<211> LENGTH: 22
<212> TYPE: DNA
<213> ORGANISM: Canis familiaris

<400> SEQUENCE: 13
tgcatgtcaa gagaggagaa tg                                              22

<210> SEQ ID NO 14
<211> LENGTH: 30
<212> TYPE: DNA
<213> ORGANISM: Canis familiaris

<400> SEQUENCE: 14
ccacttgctc atatgtacac ctgattgtcc                                      30

<210> SEQ ID NO 15
<211> LENGTH: 19
<212> TYPE: DNA
<213> ORGANISM: Canis familiaris
```

```
<400> SEQUENCE: 15
tccagcttgc agagttgtt                                                     19

<210> SEQ ID NO 16
<211> LENGTH: 101
<212> TYPE: DNA
<213> ORGANISM: Canis familiaris

<400> SEQUENCE: 16
tgcatgtcaa gagaggagaa tgtgagaatt ttaattgctc taaataaaga ccacttgctc        60
atatgtacac ctgattgtcc aaaacaactc tgcaagctgg a                           101
```

CHROMOSOMAL ASSESSMENT TO DIAGNOSE UROGENITAL MALIGNANCY IN DOGS

CROSS REFERENCE TO RELATED APPLICATIONS

This application is a § 371 U.S. National Stage of International Application PCT/US2014/65773, filed Nov. 14, 2014, which claims the benefit of U.S. Provisional Application 61/904,659 filed Nov. 15, 2013, which are hereby incorporated by reference in their entireties.

1. FIELD OF THE INVENTION

This invention relates generally to the discovery of an improved method to diagnose urogenital malignancy in dogs.

2. BACKGROUND OF THE INVENTION 2.1. Introduction

Transitional cell carcinoma (TCC), also referred to as urothelial carcinoma (UC), is the most common urinary tract neoplasm in the dog. This form of cancer may be localized in one or more anatomical sites, including the kidneys, ureters, urinary bladder, prostate, and urethra, with most cases being detected in the bladder [1]. In the bladder, the cancer develops from the transitional epithelial cells that form the lining of the bladder and invade into the bladder wall and layers of muscle. As the mass becomes larger a frequent consequence is obstruction to the flow of urine, either from the kidneys to the bladder, or from the bladder through the urethra. Pathology assessment of canine TCCs indicates that most are higher grade tumors that have the ability to spread to lymph nodes and other organs in the body (lung, liver, others).

The American Veterinary Medical Association estimates that 4.2 million dogs are diagnosed with cancer each year in the US. While precise lifetime risk and incidence numbers for TCC in the overall pet dog population is not known, TCC is estimated to represent ~1-2% of all diagnosed cancers, indicating that as many as 40,000-80,000 dogs each year could develop TCC in the US. In addition there are several breeds of purebred dog that have been reported to have an elevated risk of developing TCC of the bladder, including Scottish terrier, Shetland sheepdog, West Highland white terrier, Wire/Fox terrier and beagle.

2.2. The Diagnostic Challenge of Canine TCC

A major challenge to diagnosis of TCC in a dog is that the symptoms of urothelial cancer in the dog are shared with a variety of other urinary tract conditions. For example, bladder infections, bladder stones, hyperplastic growths in the bladder, and inflammation of the bladder can all cause symptoms in the dog similar to those resulting from a bladder cancer. Evaluation of canine urine by routine cytology may be misleading, since the non-malignant conditions above may cause shedding of abnormal looking cells in the urine, which may be mistaken for a malignancy. The use of imaging techniques, such as radiography and ultrasonography, may identify the presence of unusual growths in the urinary tract, but these may or may not be malignant, and may also result in the presence of abnormal looking cells in the urine. Presently, a confirmed diagnosis of a canine TCC may be made only following the evaluation of a biopsy of the tumor by a pathologist. Obtaining a biopsy of a probable mass in the urinary tract may be performed during surgery, cystoscopy or by traumatic catheterization, which have a decreasing level of intervention, respectively. However, any procedure that disturbs the likely tumor mass may result in seeding of malignant epithelial cells elsewhere on the local area, resulting in spreading of the cancer. The chances of 'seeding' are of concern to the clinical management. Confirmation of diagnosis of a TCC in dogs presenting with symptoms suggestive of a TCC would thus be desirable from an assessment of a free catch urine sample.

3. SUMMARY OF THE INVENTION

In particular non-limiting embodiments, the present invention provides a method for detecting a urogenital malignancy in a biological sample from a dog which comprises: (a) measuring a copy number of CFA 13, CFA 19, or CFA 36; and (b) if the copy number of CFA 13 or CFA 36 is elevated, or CFA 19 is reduced, from that of a normal control, determining that the dog has increased likelihood of the urogenital malignancy. In one embodiment, the copy number of CFA 13, CFA 19 and CFA 36 are measured.

The copy number may be measured by fluorescence in situ hybridization (FISH), polymerase chain reaction (PCR), comparative genomic hybridization (CGH), or next generation sequencing. The biological sample may be a urine sample, a fresh-frozen sample, a fresh sample, or a formalin-fixed, paraffin-embedded sample.

The invention also provides a method of selecting a dog for urogenital malignancy treatment which comprises measuring a copy number of CFA 13, CFA 19, or CFA 36 in a biological sample from a dog; and if the copy number of CFA 13 or CFA 36 is elevated, or CFA 19 is reduced, from that of a normal control, selecting the dog for urogenital malignancy treatment. The urogenital malignancy treatment may be include surgery, radiation therapy or chemotherapy.

A method of diagnosing a urogenital malignancy in a sample from a dog comprising: (a) detecting the copy number of CFA 13, CFA 19 or CFA 36 in a sample from the dog, by a nucleic acid hybridization assay with nucleic acids specific for CFA 13, CFA 19 or CFA 36; (b) comparing the detected levels to at least one sample from a training set(s), wherein a sample training set(s) comprises data from the levels from a reference sample, and the comparing step comprises applying a statistical algorithm which comprises determining a correlation between the detected levels in the sample from the subject and the detected levels from at least one training set(s); and (c) diagnosing the urogenital malignancy based on the detected levels in the sample from the subject and the results of the statistical algorithm. The nucleic acid hybridization assay may be FISH analysis.

A method of diagnosing a urogenital malignancy in a sample from a dog comprising: (a) detecting the copy number of CFA 13, CFA 19 or CFA 36 in a sample from the dog, by a digital droplet PCR assay with primers/probes specific for CFA 13, CFA 19 or CFA 36; (b) comparing the detected levels to at least one sample from a training set(s), wherein a sample training set(s) comprises data from the levels from a reference sample, and the comparing step comprises applying a statistical algorithm which comprises determining a correlation between the detected levels in the sample from the subject and the detected levels from at least one training set(s); and (c) diagnosing the urogenital malignancy based on the detected levels in the sample from the subject and the results of the statistical algorithm.

In addition, the invention provides a kit for detecting a urogenital malignancy in a dog comprising: (a) at least one reagent selected from the group consisting of: a nucleic acid probe capable of specifically detecting CFA 13, CFA 19 or CFA 36; and (b) instructions for use in measuring a copy number of CFA 13, CFA 19 or CFA 36 in a biological sample from a dog wherein if the copy number of CFA 13 or CFA 36 is elevated, or CFA 19 is reduced, from that of a normal control.

4. BRIEF DESCRIPTION OF THE FIGURES

Figure 1A:
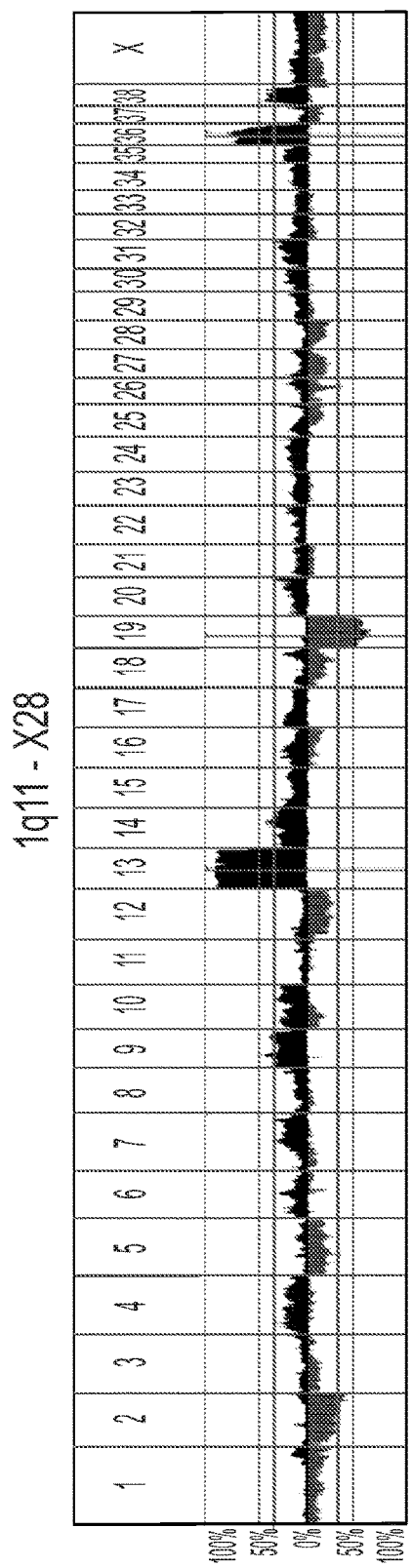
FIG. 1 shows the significant copy number variations based on analysis of 31 cases of canine TCC.

5. DETAILED DESCRIPTION OF THE INVENTION 5.1. Definitions

"Urogenital malignancy" is cancer that forms in the tissues of the bladder or neighboring tissues. Urogenital malignancy is used herein to include transitional cell carcinoma (TCC), which is also referred to as urothelial carcinoma. The methods and reagents described herein may also be used to detect squamous cell carcinoma and adenocarcinoma.

"Copy number" is a measurement of DNA, whether of a single locus, one or more loci, or an entire genome. A "copy number" of two is "wild-type" in a dog (because of diploidy, except for sex chromosomes). A "copy number" of other than two in a dog (except for sex chromosomes) deviates from wild-type. Such deviations include gains and amplifications, i.e., increases in copy numbers, and deletions, i.e., decreases in copy numbers and even the absence of copy numbers.

"Labeled," "labeled with a detectable label," and "detectably labeled" are used interchangeably herein to indicate that an entity (e.g., a probe) can be detected. "Label" and "detectable label" mean a moiety attached to an entity to render the entity detectable, such as a moiety attached to a probe to render the probe detectable upon binding to a target sequence. The moiety, itself, may not be detectable but may become detectable upon reaction with yet another moiety. Use of the term "detectably labeled" is intended to encompass such labeling.

The detectable label can be selected such that the label generates a signal, which can be measured and the intensity of which is proportional to the amount of bound entity. A wide variety of systems for labeling and/or detecting molecules, such as nucleic acids, e.g., probes, are well-known. Labeled nucleic acids can be prepared by incorporating or conjugating a label that is directly or indirectly detectable by spectroscopic, photochemical, biochemical, immunochemical, electrical, optical, chemical or other means. Suitable detectable labels include radioisotopes, fluorophores, chromophores, chemiluminescent agents, microparticles, enzymes, magnetic particles, electron dense particles, mass labels, spin labels, haptens, and the like. Fluorophores and chemiluminescent agents are preferred herein.

"Nucleic acid sample" refers to a sample comprising nucleic acid in a form suitable for hybridization with a probe, such as a sample comprising nuclei or nucleic acids isolated or purified from such nuclei. The nucleic acid sample may comprise total or partial (e.g., particular chromosome(s)) genomic DNA, total or partial mRNA (e.g., particular chromosome(s) or gene(s)), or selected sequence(s). Condensed chromosomes (such as are present in interphase or metaphase) are suitable for use as targets in in situ hybridization, such as FISH.

"Predetermined cutoff" and "predetermined level" refer generally to a cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.).

"Probe," in the context of the present disclosure, is an oligonucleotide or polynucleotide that can selectively hybridize to at least a portion of a target sequence under conditions that allow for or promote selective hybridization. In general, a probe can be complementary to the coding or sense (+) strand of DNA or complementary to the non-coding or anti-sense (−) strand of DNA (sometimes referred to as "reverse-complementary"). Probes can vary significantly in length. A length of about 10 to about 100 nucleotides, such as about 15 to about 75 nucleotides, e.g., about 15 to about 50 nucleotides, can be preferred in some applications such as PCR, whereas a length of about 50 to about $1 \times 10^6$ nucleotides can be preferred for chromosomal probes and a length of about 5,000 to about 800,000 nucleotides or more preferably about 100,000 to about 400,000 for BAC probes.

The invention encompasses fragments of a nucleic acids that can serve (1) as probes for detecting segments of domestic dog (*Canis familairis*, CFA) genome referred to as chromosomes 13, 19 or 36 (hereafter referred to as CFA 13, CFA 19 and CFA 36). The dog genome has been sequenced and is available for example, the NCBI Canis lupus familiaris genome database; or ENSEMBL database CanFam3.1 (GCA_000002285.2). See also, Lindblad-Toh et al. 2005 "Genome sequence, comparative analysis and haplotype structure of the domestic dog" *Nature* 438 (7069), 803-819.

The changes in CFA 13, 19 or 36 may be detected by a number of methods well known in the art, e.g. Southern and northern blotting, dot blotting, colony hybridizations, hybridization to an array, comparative genomic hybridization (CGH), etc. or (2) as polymerase chain reaction (PCR) primers to amplify CFA 13, 19 or 36. PCR primers can comprise, in addition to CFA 13, 19 or 36 nucleic acid sequences, other sequences such as restriction enzyme cleavage sites that facilitate the use of the amplified nucleic acid. PCR is described in the following references: Saiki et al. 1988 *Science* 239 487-491; *PCR Technology*, Erlich, ed., Stockton Press, (1989). As explained below, PCR can be useful to detect abnormally low or high levels of CFA 13, 19 or 36.

Hybridization techniques are well known in the art and are described by Sambrook, J., E. F. Fritsch, and T. Maniatis (*Molecular Cloning: A Laboratory Manual*, Cold Spring Harbor Laboratory Press, Cold Spring Harbor, N.Y., chapters 9 and 11, (1989)) and *Current Protocols in Molecular Biology* (F. M. Ausubel et al., eds., John Wiley & Sons, Inc., sections 2.10 and 6.3-6.4 (1995)), the relevant portions of which are incorporated by reference herein. Moderately stringent conditions for filter hybridizations include hybridization in about 50% formamide, 6×SSC at a temperature from about 42° C. to 55° C. and washing at about 60° C. in 0.5×SSC, 0.1% SDS. Highly stringent conditions are defined as hybridization conditions as above, but with washing at approximately 68° C. in 0.2×SSC, 0.1% SDS. SSPE (1×SSPE is 0.15 M NaCl, 10 mM $NaH_2PO_4$, and 1.26 mM EDTA, pH 7.4) can be substituted for SSC (1×SSC is 0.15 M NaCl and 1 5 mM sodium citrate) in the hybridization and wash buffers; washes, optionally at least two washes, are performed for 15 minutes after hybridization is complete.

It should be understood that the wash temperature and wash salt concentration can be adjusted as necessary to achieve a desired degree of stringency by applying the basic principles that govern hybridization reactions and duplex stability, as known to those skilled in the art and described further below (see e.g., Sambrook et al., supra). When nucleic acids of known sequence are hybridized, the hybrid length can be determined by aligning the sequences of the nucleic acids (for example, using GAP) and identifying the region or regions of optimal sequence complementarity. The hybridization temperature for hybrids anticipated to be less than 50 base pairs in length should be 5 to 10° C. less than the melting temperature (Tm) of the hybrid, where Tm is determined according to the following equations. For hybrids less than 18 base pairs in length, Tm (° C.)=2(# of A+T bases)+4(# of G+C bases). For hybrids above 18 base pairs in length, Tm (° C.)=81.5+16.6($log_{10}$[Na+])+0.41 (% G+C)−(600 N), where N is the number of bases in the hybrid, and [Na+] is the concentration of sodium ions in the hybridization buffer. Each such hybridizing nucleic acid has a length that is at least 15 nucleotides (or at least 18 nucleotides, or at least 20, or at least 25, or at least 30, or at least 40, or at least 50, or at least 100. Sambrook et al., supra.

5.2. Polynucleotide Amplification and Determination

In many instances, it is desirable to amplify a nucleic acid sequence using any of several nucleic acid amplification procedures which are well known in the art. Specifically, nucleic acid amplification is the chemical or enzymatic synthesis of nucleic acid copies which contain a sequence that is complementary to a nucleic acid sequence being amplified (template). The methods and kits of the invention may use any nucleic acid amplification or detection methods known to one skilled in the art, such as those described in U.S. Pat. No. 5,525,462 (Takarada et al.); U.S. Pat. No. 6,114,117 (Hepp et al.); U.S. Pat. No. 6,127,120 (Graham et al.); U.S. Pat. No. 6,344,317 (Urnovitz); U.S. Pat. No. 6,448,001 (Oku); U.S. Pat. No. 6,528,632 (Catanzariti et al.); and PCT Pub. No. WO 2005/111209 (Nakajima et al.); all of which are incorporated herein by reference in their entirety.

Commonly used methods known in the art for the quantification of mRNA expression in a sample include northern blotting and in situ hybridization (Parker and Barnes, *Methods Mol. Biol.* 106:247-83, 1999), RNAse protection assays (Hod, *Biotechniques* 13:852-54, 1992), PCR-based methods, such as reverse transcription PCR(RT-PCR) (Weis et al., *TIG* 8:263-64, 1992), and array-based methods (Schena et al., *Science* 270:467-70, 1995). Alternatively, antibodies may be employed that can recognize specific duplexes, including DNA duplexes, RNA duplexes, and DNA-RNA hybrid duplexes, or DNA-protein duplexes. Representative methods for sequencing-based gene expression analysis include Serial Analysis of Gene Expression (SAGE), bead-based technologies, single molecule fluorescence in situ hybridization (smFISH) studies, and gene expression analysis by massively parallel signature sequencing. Velculescu et al. 1995 *Science* 270 484-487; Streefkerk et al., 1976, *Pro Biol Fluid Proc Coll* 24 811-814; Soini U.S. Pat. No. 5,028,545; smFISH, Lyubimova et al. 2013 *Nat Protocol* 8(9) 1743-1758.

In some embodiments, the nucleic acids are amplified by PCR amplification using methodologies known to one skilled in the art. One skilled in the art will recognize, however, that amplification can be accomplished by any known method, such as ligase chain reaction (LCR), Qβ-replicase amplification, rolling circle amplification, transcription amplification, self-sustained sequence replication, nucleic acid sequence-based amplification (NASBA), each of which provides sufficient amplification. Branched-DNA technology may also be used to qualitatively demonstrate the presence of a sequence of the technology, which represents a particular methylation pattern, or to quantitatively determine the amount of this particular genomic sequence in a sample. Nolte reviews branched-DNA signal amplification for direct quantitation of nucleic acid sequences in clinical samples (Nolte, 1998, *Adv. Clin. Chem.* 33:201-235).

The PCR process is well known in the art and is thus not described in detail herein. For a review of PCR methods and protocols, see, e.g., Innis et al., eds., *PCR Protocols, A Guide to Methods and Application*, Academic Press, Inc., San Diego, Calif. 1990; U.S. Pat. No. 4,683,202 (Mullis); which are incorporated herein by reference in their entirety. PCR reagents and protocols are also available from commercial vendors, such as Roche Molecular Systems. PCR may be carried out as an automated process with a thermostable enzyme. In this process, the temperature of the reaction mixture is cycled through a denaturing region, a primer annealing region, and an extension reaction region automatically. Machines specifically adapted for this purpose are commercially available.

5.3. High Throughput, Single Molecule Sequencing, and Direct Detection Technologies Suitable next generation sequencing technologies are widely available. Examples include the 454 Life Sciences platform (Roche, Branford, Conn.) (Margulies et al. 2005 *Nature*, 437, 376-380); lllumina's Genome Analyzer, GoldenGate Methylation Assay, or Infinium Methylation Assays, i.e., Infinium HumanMethylation 27K BeadArray or Vera-Code GoldenGate methylation array (Illumina, San Diego, Calif.; Bibkova et al., 2006, *Genome Res.* 16, 383-393; U.S. Pat. Nos. 6,306,597 and 7,598,035 (Macevicz); U.S. Pat. No. 7,232,656 (Balasubramanian et al.)); or DNA Sequencing by Ligation, SOLiD System (Applied Biosystems/Life Technologies; U.S. Pat. Nos. 6,797,470, 7,083,917, 7,166, 434, 7,320,865, 7,332,285, 7,364,858, and 7,429,453 (Barany et al.); or the Helicos True Single Molecule DNA sequencing technology (Harris et al., 2008 *Science*, 320, 106-109; U.S. Pat. Nos. 7,037,687 and 7,645,596 (Williams et al.); U.S. Pat. No. 7,169,560 (Lapidus et al.); U.S. Pat. No. 7,769,400 (Harris)), the single molecule, real-time (SMRT™) technology of Pacific Biosciences, and sequencing (Soni and Meller, 2007, *Clin. Chem.* 53, 1996-2001) which are incorporated herein by reference in their entirety. These systems allow the sequencing of many nucleic acid molecules isolated from a specimen at high orders of multiplexing in a parallel fashion (Dear, 2003, *Brief Funct. Genomic Proteomic,* 1(4), 397-416 and McCaughan and Dear, 2010, *J. Pathol.*, 220, 297-306). Each of these platforms allow sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Study nucleic acids may be immobilized to a solid support, hybridized with a sequencing primer, incubated with DNA polymerase, ATP sulfurylase, luciferase, apyrase, adenosine 5' phosphsulfate and luciferin. Nucleotide solutions are sequentially added and removed. Correct incorporation of a nucleotide releases a pyrophosphate, which interacts with ATP sulfurylase and produces ATP in the presence of adenosine 5' phosphsulfate, fueling the luciferin reaction, which produces a chemiluminescent signal allowing sequence determination. Machines for pyrosequencing and methylation specific reagents are available from Qiagen, Inc. (Valencia, Calif.). See also Tost and Gut, 2007, *Nat. Prot.* 2 2265-2275. An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleotide sequences by pyrosequencing methodology (e.g., Nakano et al., 2003, *J. Biotech.* 102, 117-124). Such a system can be used to exponentially amplify amplification products generated by a process described herein, e.g., by ligating a heterologous nucleic acid to the first amplification product generated by a process described herein.

Certain single-molecule sequencing embodiments are based on the principal of sequencing by synthesis, and utilize single-pair Fluorescence Resonance Energy Transfer (single pair FRET) as a mechanism by which photons are emitted as a result of successful nucleotide incorporation. The emitted photons often are detected using intensified or high sensitivity cooled charge-couple-devices in conjunction with total internal reflection microscopy (TIRM). Photons are only emitted when the introduced reaction solution contains the correct nucleotide for incorporation into the growing nucleic acid chain that is synthesized as a result of the sequencing process. In FRET based single-molecule sequencing or detection, energy is transferred between two fluorescent dyes, sometimes polymethine cyanine dyes Cy3 and Cy5, through long-range dipole interactions. The donor is excited at its specific excitation wavelength and the excited state energy is transferred, non-radiatively to the acceptor dye, which in turn becomes excited. The acceptor dye eventually returns to the ground state by radiative emission of a photon. The two dyes used in the energy transfer process represent the "single pair", in single pair FRET. Cy3 often is used as the donor fluorophore and often is incorporated as the first labeled nucleotide. Cy5 often is used as the acceptor fluorophore and is used as the nucleotide label for successive nucleotide additions after incorporation of a first Cy3 labeled nucleotide. The fluorophores generally are within 10 nanometers of each other for energy transfer to occur successfully. Bailey et al. recently reported a highly sensitive (15 pg methylated DNA) method using quantum dots to detect methylation status using fluorescence resonance energy transfer (MS-qFRET) (Bailey et al. 2009, *Genome Res.* 19(8), 1455-1461, which is incorporated herein by reference in its entirety).

An example of a system that can be used based on single-molecule sequencing generally involves hybridizing a primer to a study nucleic acid to generate a complex; associating the complex with a solid phase; iteratively extending the primer by a nucleotide tagged with a fluorescent molecule; and capturing an image of fluorescence resonance energy transfer signals after each iteration (e.g., Braslaysky et al., *PNAS* 100(7): 3960-3964 (2003); U.S. Pat. No. 7,297,518 (Quake et al.) which are incorporated herein by reference in their entirety). Such a system can be used to directly sequence amplification products generated by processes described herein. In some embodiments the released linear amplification product can be hybridized to a primer that contains sequences complementary to immobilized capture sequences present on a solid support, a bead or glass slide for example. Hybridization of the primer-released linear amplification product complexes with the immobilized capture sequences, immobilizes released linear amplification products to solid supports for single pair FRET based sequencing by synthesis. The primer often is fluorescent, so that an initial reference image of the surface of the slide with immobilized nucleic acids can be generated. The initial reference image is useful for determining locations at which true nucleotide incorporation is occurring. Fluorescence signals detected in array locations not initially identified in the "primer only" reference image are discarded as non-specific fluorescence. Following immobilization of the primer-released linear amplification product complexes, the bound nucleic acids often are sequenced in parallel by the iterative steps of, a) polymerase extension in the presence of one fluorescently labeled nucleotide, b) detection of fluorescence using appropriate microscopy, TIRM for example, c) removal of fluorescent nucleotide, and d) return to step a with a different fluorescently labeled nucleotide.

The technology may be practiced with digital PCR. Digital PCR was developed by Kalinina and colleagues (Kalinina et al., 1997, *Nucleic Acids Res.* 25; 1999-2004) and further developed by Vogelstein and Kinzler (1999, *Proc. Natl. Acad. Sci. U.S.A.* 96; 9236-9241). The application of digital PCR is described by Cantor et al. (PCT Pub. Nos. WO 2005/023091A2 (Cantor et al.); WO 2007/092473 A2, (Quake et al.)), which are hereby incorporated by reference in their entirety. Digital PCR takes advantage of nucleic acid (DNA, cDNA or RNA) amplification on a single molecule level, and offers a highly sensitive method for quantifying low copy number nucleic acid. Fluidigm® Corporation, BioRad's Digital PCR and Raindance technologies all offer systems for the digital analysis of nucleic acids. See, Karlin-Neumann G et al. (2012). Probing copy number variations using Bio-Rad's QX100/200™ Droplet Digital™ PCR system. Bio-Rad Bulletin 6277; Diderot et al., *Clinical Chemistry* February 2013 clinchem.2012.193409.

In some embodiments, nucleotide sequencing may be by solid phase single nucleotide sequencing methods and processes. Solid phase single nucleotide sequencing methods involve contacting sample nucleic acid and solid support under conditions in which a single molecule of sample nucleic acid hybridizes to a single molecule of a solid support. Such conditions can include providing the solid support molecules and a single molecule of sample nucleic acid in a "microreactor." Such conditions also can include providing a mixture in which the sample nucleic acid molecule can hybridize to solid phase nucleic acid on the solid support. Single nucleotide sequencing methods useful in the embodiments described herein are described in PCT Pub. No. WO 2009/091934 (Cantor).

In certain embodiments, nanopore sequencing detection methods include (a) contacting a nucleic acid for sequencing ("base nucleic acid," e.g., linked probe molecule) with sequence-specific detectors, under conditions in which the detectors specifically hybridize to substantially complementary subsequences of the base nucleic acid; (b) detecting signals from the detectors and (c) determining the sequence of the base nucleic acid according to the signals detected. In certain embodiments, the detectors hybridized to the base nucleic acid are disassociated from the base nucleic acid (e.g., sequentially dissociated) when the detectors interfere with a nanopore structure as the base nucleic acid passes through a pore, and the detectors disassociated from the base sequence are detected.

A detector also may include one or more regions of nucleotides that do not hybridize to the base nucleic acid. In some embodiments, a detector is a molecular beacon. A detector often comprises one or more detectable labels independently selected from those described herein. Each detectable label can be detected by any convenient detection process capable of detecting a signal generated by each label (e.g., magnetic, electric, chemical, optical and the like). For example, a CD camera can be used to detect signals from one or more distinguishable quantum dots linked to a detector.

Next generation sequencing techniques may be applied to measure expression levels or count numbers of transcripts using RNA-seq or whole transcriptome shotgun sequencing. See, e.g., Mortazavi et al. 2008 *Nat Meth* 5(7) 621-627 or Wang et al. 2009 *Nat Rev Genet* 10(1) 57-63.

Nucleic acids in the invention may be counted using methods known in the art. In one embodiment, NanoString's nCounter system may be used. Geiss et al. 2008 *Nat Biotech* 26(3) 317-325; U.S. Pat. No. 7,473,767 (Dimitrov). Alternatively, Fluidigm's Dynamic Array system may be used. Byrne et al. 2009 *PLoS ONE* 4 e7118; Helzer et al. 2009 *Can Res* 69 7860-7866. For reviews, see also Zhao et al. 2011 *Sci China Chem* 54(8) 1185-1201 and Ozsolak and Milos 2011 *Nat Rev Genet* 12 87-98.

The invention encompasses any method known in the art for enhancing the sensitivity of the detectable signal in such assays, including, but not limited to, the use of cyclic probe technology (Bakkaoui et al., 1996, *BioTechniques* 20: 240-8, which is incorporated herein by reference in its entirety); and the use of branched probes (Urdea et al., 1993, *Clin. Chem.* 39, 725-6; which is incorporated herein by reference in its entirety). The hybridization complexes are detected according to well-known techniques in the art.

Reverse transcribed or amplified nucleic acids may be modified nucleic acids. Modified nucleic acids can include nucleotide analogs, and in certain embodiments include a detectable label and/or a capture agent. Examples of detectable labels include, without limitation, fluorophores, radioisotopes, colorimetric agents, light emitting agents, chemiluminescent agents, light scattering agents, enzymes and the like. Examples of capture agents include, without limitation, an agent from a binding pair selected from antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) pairs, and the like. Modified nucleic acids having a capture agent can be immobilized to a solid support in certain embodiments.

The invention described herein may be used in conjunction with other molecular techniques for detection of cancer such as US Pat Pub 2013/0171637 (Giafis et al.) the contents of which are hereby incorporated by reference in its entirety.

5.4. Statistical Methods

The data may be ranked for its ability to distinguish biomarkers in both the 1 versus all (i.e., disease versus normal) and the all-pairwise (i.e., normal versus specific disease) cases. One statistic used for the ranking is the area under the receiver operator characteristic (ROC) curve (a plot of sensitivity versus (1-specificity)). Although biomarkers are evaluated for reliability across datasets, the independent sample sets are not combined for the purposes of the ROC ranking. As a result, multiple independent analyses are performed and multiple independent rankings are obtained for each biomarker's ability to distinguish groups of interest.

It is to be understood that other genes and/or diagnostic criteria may be used in this invention. For example, animal characteristics, standard blood workups, the results of imaging tests, and/or histological evaluation may optionally be combined with biomarkers disclosed herein.

Such analysis methods may be used to form a predictive model, and then use that model to classify test data. For example, one convenient and particularly effective method of classification employs multivariate statistical analysis modeling, first to form a model (a "predictive mathematical model") using data ("modeling data") from samples of known class (e.g., from subjects known to have, or not have, a particular class, subclass or grade of lung cancer), and second to classify an unknown sample (e.g., "test data"), according to lung cancer status.

Pattern recognition (PR) methods have been used widely to characterize many different types of problems ranging for example over linguistics, fingerprinting, chemistry and psychology. In the context of the methods described herein, pattern recognition is the use of multivariate statistics, both parametric and non-parametric, to analyze spectroscopic data, and hence to classify samples and to predict the value of some dependent variable based on a range of observed measurements. There are two main approaches. One set of methods is termed "unsupervised" and these simply reduce data complexity in a rational way and also produce display plots which can be interpreted by the human eye. The other approach is termed "supervised" whereby a training set of samples with known class or outcome is used to produce a mathematical model and is then evaluated with independent validation data sets.

Unsupervised PR methods are used to analyze data without reference to any other independent knowledge. Examples of unsupervised pattern recognition methods include principal component analysis (PCA), hierarchical cluster analysis (HCA), and non-linear mapping (NLM).

Alternatively, and in order to develop automatic classification methods, it has proved efficient to use a "supervised" approach to data analysis. Here, a "training set" of biomarker expression data is used to construct a statistical model that predicts correctly the "class" of each sample. This training set is then tested with independent data (referred to as a test or validation set) to determine the robustness of the computer-based model. These models are sometimes termed "expert systems," but may be based on a range of different mathematical procedures. Supervised methods can use a data set with reduced dimensionality (for example, the first few principal components), but typically use unreduced data, with all dimensionality. In all cases the methods allow the quantitative description of the multivariate boundaries that characterize and separate each class, for example, each class of lung cancer in terms of its biomarker expression profile. It is also possible to obtain confidence limits on any predictions, for example, a level of probability to be placed on the goodness of fit (see, for example, Sharaf;

Illman; Kowalski, eds. (1986). Chemometrics. New York: Wiley). The robustness of the predictive models can also be checked using cross-validation, by leaving out selected samples from the analysis.

Examples of supervised pattern recognition methods include the following nearest centroid methods (Dabney 2005 *Bioinformatics* 21(22):4148-4154 and Tibshirani et al. 2002 *Proc. Natl. Acad. Sci. USA* 99(10):6576-6572); soft independent modeling of class analysis (SIMCA) (see, for example, Wold, (1977) Chemometrics: theory and application 52: 243-282.); partial least squares analysis (PLS) (see, for example, Wold (1966) Multivariate analysis 1: 391-420; Joreskog (1982) Causality, structure, prediction 1: 263-270); linear discriminant analysis (LDA) (see, for example, Nillson (1965). Learning machines. New York.); K-nearest neighbor analysis (KNN) (see, for example, Brown and Martin 1996 *J Chem Info Computer Sci* 36(3):572-584); artificial neural networks (ANN) (see, for example, Wasserman (1993). Advanced methods in neural computing. John Wiley & Sons, Inc; O'Hare & Jennings (Eds.). (1996). Foundations of distributed artificial intelligence (Vol. 9). Wiley); probabilistic neural networks (PNNs) (see, for example, Bishop & Nasrabadi (2006). Pattern recognition and machine learning (Vol. 1, p. 740). New York: Springer; Specht, (1990). Probabilistic neural networks. Neural networks, 3(1), 109-118); rule induction (RI) (see, for example, Quinlan (1986) Machine learning, 1(1), 81-106); and, Bayesian methods (see, for example, Bretthorst (1990). An introduction to parameter estimation using Bayesian probability theory. In Maximum entropy and Bayesian methods (pp. 53-79). Springer Netherlands; Bretthorst, G. L. (1988). Bayesian spectrum analysis and parameter estimation (Vol. 48). New York: Springer-Verlag); unsupervised hierarchical clustering (see for example Herrero 2001 *Bioinformatics* 17(2) 126-136). In one embodiment, the classifier is the centroid based method described in Mullins et al. 2007 *Clin Chem* 53(7):1273-9, which is herein incorporated by reference in its entirety for its teachings regarding disease classification.

It is often useful to pre-process data, for example, by addressing missing data, translation, scaling, weighting, etc. Multivariate projection methods, such as principal component analysis (PCA) and partial least squares analysis (PLS), are so-called scaling sensitive methods. By using prior knowledge and experience about the type of data studied, the quality of the data prior to multivariate modeling can be enhanced by scaling and/or weighting. Adequate scaling and/or weighting can reveal important and interesting variation hidden within the data, and therefore make subsequent multivariate modeling more efficient. Scaling and weighting may be used to place the data in the correct metric, based on knowledge and experience of the studied system, and therefore reveal patterns already inherently present in the data.

If possible, missing data, for example gaps in column values, should be avoided. However, if necessary, such missing data may replaced or "filled" with, for example, the mean value of a column ("mean fill"); a random value ("random fill"); or a value based on a principal component analysis ("principal component fill"). Each of these different approaches will have a different effect on subsequent PR analysis.

"Translation" of the descriptor coordinate axes can be useful. Examples of such translation include normalization and mean centering. "Normalization" may be used to remove sample-to-sample variation. Many normalization approaches are possible, and they can often be applied at any of several points in the analysis. "Mean centering" may be used to simplify interpretation. Usually, for each descriptor, the average value of that descriptor for all samples is subtracted. In this way, the mean of a descriptor coincides with the origin, and all descriptors are "centered" at zero. In "unit variance scaling," data can be scaled to equal variance. Usually, the value of each descriptor is scaled by 1/StDev, where StDev is the standard deviation for that descriptor for all samples. "Pareto scaling" is, in some sense, intermediate between mean centering and unit variance scaling. In pareto scaling, the value of each descriptor is scaled by 1/sqrt (StDev), where StDev is the standard deviation for that descriptor for all samples. In this way, each descriptor has a variance numerically equal to its initial standard deviation. The pareto scaling may be performed, for example, on raw data or mean centered data.

"Logarithmic scaling" may be used to assist interpretation when data have a positive skew and/or when data spans a large range, e.g., several orders of magnitude. Usually, for each descriptor, the value is replaced by the logarithm of that value. In "equal range scaling," each descriptor is divided by the range of that descriptor for all samples. In this way, all descriptors have the same range, that is, 1. However, this method is sensitive to presence of outlier points. In "autoscaling," each data vector is mean centred and unit variance scaled. This technique is a very useful because each descriptor is then weighted equally and large and small values are treated with equal emphasis. This can be important for analytes present at very low, but still detectable, levels.

Several supervised methods of scaling data are also known. Some of these can provide a measure of the ability of a parameter (e.g., a descriptor) to discriminate between classes, and can be used to improve classification by stretching a separation. For example, in "variance weighting," the variance weight of a single parameter (e.g., a descriptor) is calculated as the ratio of the inter-class variances to the sum of the intra-class variances. A large value means that this variable is discriminating between the classes. For example, if the samples are known to fall into two classes (e.g., a training set), it is possible to examine the mean and variance of each descriptor. If a descriptor has very different mean values and a small variance, then it will be good at separating the classes. "Feature weighting" is a more general description of variance weighting, where not only the mean and standard deviation of each descriptor is calculated, but other well-known weighting factors, such as the Fisher weight, are used.

The methods described herein may be implemented and/or the results recorded using any device capable of implementing the methods and/or recording the results. Examples of devices that may be used include but are not limited to electronic computational devices, including computers of all types. When the methods described herein are implemented and/or recorded in a computer, the computer program that may be used to configure the computer to carry out the steps of the methods may be contained in any computer readable medium capable of containing the computer program. Examples of computer readable medium that may be used include but are not limited to diskettes, CD-ROMs, DVDs, ROM, RAM, and other memory and computer storage devices. The computer program that may be used to configure the computer to carry out the steps of the methods and/or record the results may also be provided over an electronic network, for example, over the internet, an intranet, or other network.

The process of comparing a measured value and a reference value can be carried out in any convenient manner appropriate to the type of measured value and reference value for the discriminative gene at issue. "Measuring" can be performed using quantitative or qualitative measurement techniques, and the mode of comparing a measured value and a reference value can vary depending on the measurement technology employed. For example, when a qualitative colorimetric assay is used to measure expression levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device). However, it is expected that the measured values used in the methods of the invention will most commonly be quantitative values. In other examples, measured values are qualitative. As with qualitative measurements, the comparison can be made by inspecting the numerical data, or by inspecting representations of the data (e.g., inspecting graphical representations such as bar or line graphs).

The process of comparing may be manual (such as visual inspection by the practitioner of the method) or it may be automated. For example, an assay device (such as a luminometer for measuring chemiluminescent signals) may include circuitry and software enabling it to compare a measured value with a reference value for a biomarker protein. Alternately, a separate device (e.g., a digital computer) may be used to compare the measured value(s) and the reference value(s). Automated devices for comparison may include stored reference values for the biomarker protein(s) being measured, or they may compare the measured value(s) with reference values that are derived from contemporaneously measured reference samples (e.g., samples from control subjects).

As will be apparent to those of skill in the art, when replicate measurements are taken, the measured value that is compared with the reference value is a value that takes into account the replicate measurements. The replicate measurements may be taken into account by using either the mean or median of the measured values as the "measured value."

The invention also includes methods of identifying animals for particular treatments or selecting animals for which a particular treatment would be desirable or contraindicated.

The methods above may be performed by a reference laboratory, a veterinary hospital pathology laboratory, a university veterinary laboratory, a veterinarian's office or a veterinarian. The methods above may further comprise an algorithm and/or statistical analysis.

5.5. Samples

The sample may be a urine sample, a tissue sample, a blood sample, a cell free extract of blood, plasma, serum, urine. For the cytogenetic assays, as shown the examples, cells are used to provide templates for the FISH probes. For PCR assays, tumor DNA may be obtained from cells or cell-free plasma/serum/urine.

5.6. Compositions and Kits

The invention provides compositions and kits for detecting urogenital malignancy in a dog comprising: (a) at least one reagent selected from the group consisting of: a nucleic acid probe capable of specifically detecting CFA 13, CFA 19 or CFA 36; and (b) instructions for use in measuring a copy number of CFA 13, CFA 19 or CFA 36 in a biological sample from a dog wherein if the copy number of CFA 13 or CFA 36 is elevated, or CFA 19 is reduced, from that of a normal control.

The instructions comprise determining in a sample of relevant cells obtained from the dog the presence of chromosomal abnormalities, wherein the presence of chromosomal abnormalities involving at least two of the probes indicates that the patient has bladder cancer. Such kits may further comprise, or consist of, blocking agents or other probes, various labels or labeling agents to facilitate detection of the probes, reagents for hybridization (e.g., buffers), a metaphase spread, and the like.

Unless defined otherwise, all technical and scientific terms used herein have the same meaning as commonly understood by one of ordinary skill in the art to which this invention belongs. The article "a" and "an" are used herein to refer to one or more than one (i.e., to at least one) of the grammatical object(s) of the article. By way of example, "an element" means one or more elements.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The following Examples further illustrate the invention and are not intended to limit the scope of the invention. In particular, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

6. EXAMPLES

6.1. Experimental Data

Primary tumor biopsy samples (n=31) were collected from untreated dogs with TCC and either fixed in formalin or snap frozen prior to being stored in liquid nitrogen. In addition non-neoplastic bladder tissues were collected at North Carolina State University College of Veterinary Medicine during necropsy of dogs with no signs of clinical disease. Control specimens were assessed by a veterinary pathologist and confirmed to be histopathologically 'normal' with no signs of neoplasia.

6.2. oaCGH

DNA was extracted from tumors and verified to be high molecular weight upon agarose gel electrophoresis and with spectrophotometer readings of 260:230>2 and 260:280>1.8 (Nanodrop-1000, Nanodrop). DNA isolated from each of the primary tumor biopsies (test samples) and labeled using the Genomic DNA Enzymatic Labeling Kit (Agilent) to incorporate a fluorophore-conjugated dNTP, as described previously [2]. Gender specific reference DNA samples were generated from mixed breed dogs, pooling equimolar quantities of DNA from 10 healthy males and 10 healthy females and labeled similarly but with a different fluorophore-conjugate dNTP. Fluorescently labeled test and reference samples were hybridized to Canine G3 Sureprint 180,000 feature oligonucleotide-array-cCGH (oaCGH) arrays (Agilent, AMADID 025522) for 40 hours at 65° C. and 20 rpm, as described previously [3]. Arrays were scanned at 3 µm using a high-resolution microarray scanner (Agilent, Model G2505C) and data extracted using Feature Extraction (v10.9) software. Scan data were assessed for data quality by the 'Quality Metrics' report in Agilent's Feature extraction software (v10.5)(Agilent Technologies). FASST2 Segmentation Algorithm, a Hidden Markov Model (HMM) based approach, was used to make copy number calls. The FASST2 algorithm, unlike other common HMM methods for copy number estimation, does not aim to estimate the copy number state at each probe but uses many states to cover more possibilities, such as mosaic events. These state values are then used to make calls based on a log-ratio threshold. The significance threshold for segmentation was set at $5\times10^{-6}$, also requiring a minimum of three probes per segment and a maximum probe spacing of 1 Mb between adjacent probes before breaking a segment. The log ratio thresholds for single copy gain and single copy loss were set at +0.201 and −0.234, respectively.

DNA copy number aberrations 'called' by the FASST2 segmentation algorithm were compared between the cohorts of confirmed cases TCC (n=31) and clinical, healthy specimens (n>100). CGH results were analyzed using Nexus DNA Copy Number Discovery (V7). to identify recurrent aberrations in the cell population from which genomic DNA was isolated; detectable aberrations represent the mean DNA copy number of genomic segments within that population of cells. Chromosomes with the highest levels of recurrent DNA copy number changes in TCC identified by CGH were subsequently assessed for copy number status in individual cells obtained from urine specimens of canine patients presenting with confirmed TCC as well as from dogs that were clinical health and presented with no evidence of a malignancy.

6.3. Results

Genome-wide oaCGH data of DNA derived from biopsy specimens obtained from 31 primary canine TCC cases revealed numerous copy number aberrations across the canine genome, combinations of which could be used to develop an assay to detect the presence of aberrations consistent with the presentation of a TCC (FIG. 1).

Figure 1B:
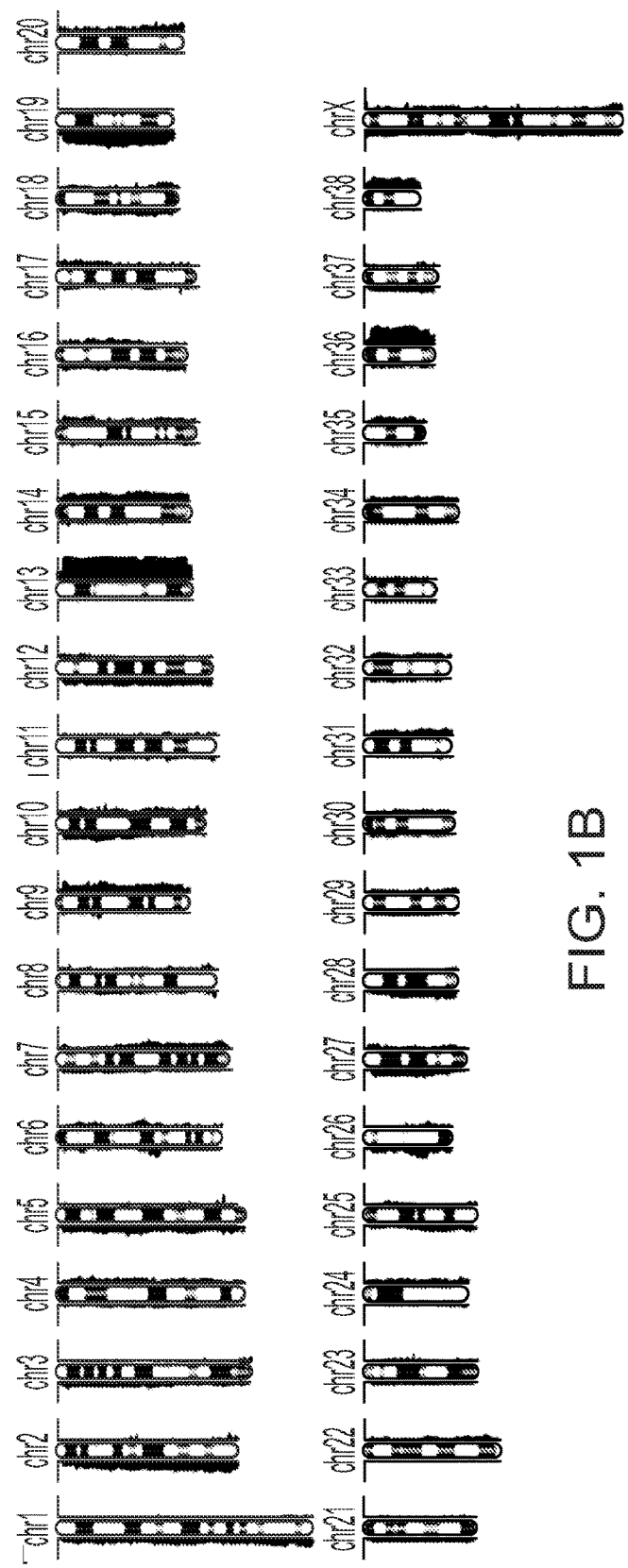
Figure 1C:
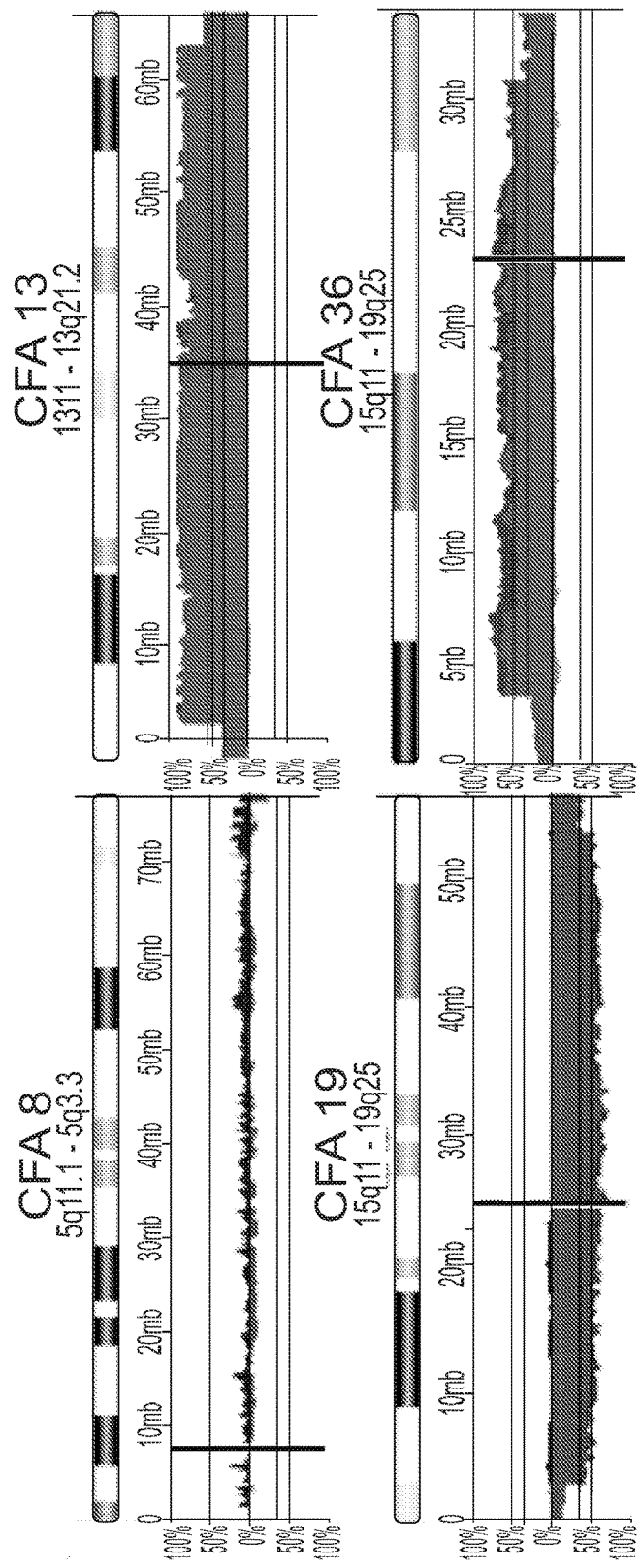

FIG. 1. Frequency of significant DNA copy number changes in 31 cases of canine TCC. A) Genome-wide penetrance plot showing the distribution and frequency of DNA copy number changes at (26 kb resolution). The x-axis shows the genome of the domestic dog partitioned into the 38 autosomes and the X chromosome. The y-axis shows the proportion of the 31 cases that presented with a copy number aberration at each of the genome intervals detected by the oaCGH platform used (smallest interval ~26 kb). Dark gray bars above 0% indicate the percentage of cases presenting with DNA copy number increase and light gray bars below 0% indicate the percentage of cases presenting with DNA copy number loss, at each of the segmented regions. It is clear that there are numerous whole chromosome and chromosomal segments that present with a level of copy number aberration in the cohort evaluated. Any of these regions could be used to detect the presence abnormal cells in patients suspected of presenting with a uriogenital malignancy. The highest frequency aberrations (>75% of cases) involved DNA copy number increase of CFA 13 and 36 and DNA copy number loss of CFA 19. A second tier of recurrent copy number changes (where frequency is >33% of cases, represented by the thicker black horizontal line) are evident as copy number loss of regions of CFA 2, 5, 6, 10, 12, 26, 27, 28 and X, and copy number involving regions of CFA 2, 4, 5, 6, 7, 10, 14, 17, 20, 23, 24, 30, 31, 35, 38 and X. For the three most recurrent aberrations (gain of 13, loss of 19 and gain of 36), example peaks of aberration frequency representing ~1 Mb intervals (detected by the specific oaCGH platform used) are shown by the vertical grey lines on CFA 13, 19 and 36. In addition the region of CFA 8 bisected by a grey vertical line represents the region of the genome where no detectable significant copy changes were evident in all 31 cases of TCC. FIG. 1B) Penetrance data presented in a conventional cytogenetic ideogram of the canine karyotype to provide an alternate representation of the chromosomes and chromosomal regions subject to DNA copy number gain (histograms to the right of a chromosome) and loss (histograms to the left of each chromosome). FIG. 1C) Individual chromosome penetrance plots showing the frequency of DNA copy number changes along the lengths of CFA 8, 13, 19 and 38. The same grey vertical lines indicated in panel A are retained for each individual chromosome to represent selected regions of each chromosome where the frequency of the aberration is highest, for CFA 13, 19 and 38, and where no copy number changes were detected in any of the 31 cases on CFA 8. The example 1 Mb sized peaks of aberration frequency (indicated by FASST2 analysis of log 2 ratios) indicated on CFA 13, 19 and 36 are centered at chr13:35-36 Mb, chr19:25-26 Mb and chr36:23-24 Mb, and the region of CFA8 that was copy number neutral when assessed by FASST2 analysis of log 2 ratio data was located at chr8:7-8 Mb using canfam2 locations.

For the three chromosomes with the highest frequency of aneuploidy, represented by gain of dog chromosome (CFA) 13, deletion of CFA 19, and gain of CFA 36, the frequencies of these changes in the samples evaluated are shown in Table 1. Analysis of over 100 cases of non-neoplastic specimens from dogs indicated no detectable copy number changes of each of CFA 13, CFA 19 and CFA 36 for this sample set. These data therefore provide a means to determine the presence of abnormal cells based on detection and enumeration of one or more of these three chromosomes.

TABLE 1

Frequency of categorical (neutral, loss or gain) copy number status of dog chromosomes 13, 19 and 31 in cases and controls, determined by analysis of DNA samples isolated form biopsy specimens of 31 cases of confirmed canine TCC and >100 cases of non-malignant cells. The expected copy number of all three of these chromosomes is n = 2 (neutral), as evident by analysis of cells from healthy dogs. The copy number changes detected for CFA 13, 19 and 36 were unidirectional, with CFA 13 and 36 present as additional copies and CFA 19 presented with reduced copies.

TCC 'cases' (n = 31)  Frequency of copy number status

| Chromosome | gain (n > 2) | loss (n < 2) | neutral (n = 2) |
|---|---|---|---|
| CFA 13 | 96.77% | 0.00% | 3.23% |
| CFA 19 | 0.00% | 77.42% | 22.58% |
| CFA 36 | 83.87% | 0.00% | 16.13% |

Normal 'controls' (n > 100)

| Chromosome | gain (n > 2) | loss (n < 2) | neutral (n = 2) |
|---|---|---|---|
| CFA 13 | 0.00% | 0.00% | 100.00% |
| CFA 19 | 0.00% | 0.00% | 100.00% |
| CFA 36 | 0.00% | 0.00% | 100.00% |

Table 2 shows additional data regarding the 31 samples.

TABLE 2

Combined frequencies of copy number gain of 36, and 19 and loss of 19 in 31 cases of canine TCC.

| Aberration in each case | Number | proportion | % age |
|---|---|---|---|
| +13 and −19 and +36 | 21 | 21/31 | 67.74% |
| +13 and −19 only | 2 | 2/31 | 6.45% |
| +13 and +36 only | 5 | 5/31 | 16.13% |
| −19 and +36 only | 1 | 1/31 | 3.23% |
| +13 only | 2 | 2/31 | 6.45% |
| TOTAL | 31 | | 100.00% | these data show that
100% of TCC have one or more of the three aberrations
93.55% of TCC have two or more of the three aberrations
67.74% of TCC have all three of the aberrations 6.4. Statistical analysis Analysis of several hundred DNA samples from pathologically verified non-neoplastic tissue (controls) indicated that none of CFA 13, CFA 19 and CFA 36 demonstrated copy number aberration. As such the sensitivity, specificity, % correctly classified, and the AUC values (with 95% CI) for each of the three regions were calculated, based on the presence of at least 100 totally negative controls.

Using the frequencies provided in Table 1 for the aneuploidy of dog chromosomes 13, 19 and 36 in canine TCC, measures of association and potential predictive performance were calculated for each of three aberrations.

Several statistical measures were calculated.

First, the relative risk (RR) was calculated. As calculated, the risk ratio can be interpreted as the overall risk of a dog presenting with neoplastic cells detectable (in either a bladder tumor biopsy or a urine sample from a suspected cases of TCC) given that it has gain of CFA 13 and/or gain of CFA 36 and/or loss of CFA 19, compared to the overall risk that a dog does not have neoplastic cells. Relative risk (RR) is simply the probability or relationship between two events. For example, a relative risk of 10 would indicate that patient from which the specimen was obtained would be 10 times more likely to have a urinary tract neoplasm/TCC than not.

Second, the odds ratio (OR) was calculated. As calculated, the odds ratio can be interpreted as the odds of a dog presenting with a malignancy/TCC, given that it has aneuploidy of the chromosome evaluated, compared to the odds that a dog does not have a malignancy/TCC given that it has aneuploidy of the chromosome evaluated. Instead of using pure percentages (as for RR), OR uses the ratio of odds. The OR explains the 'odds' not in its colloquial definition (i.e. chance) but rather on its statistical definition, which is the probability of an event over (divided by) the probability of a certain event not happening.

Third, the sensitivity and specificity were calculated to determine likelihood of false positives and false negatives. Sensitivity measures the proportion of actual positives that are correctly identified as such (in this case the percentage of confirmed cases of TCC correctly identified). Specificity measures the proportion of negatives that are correctly identified, in this case the percentage of confirmed non-TCC bearing dogs correctly identified.

Fourth, an overall misclassification rate was calculated. This measure tells the percentage of dogs that are misclassified by this marker. The accuracy of the test overall would simply be one minus (1−) the misclassification rate.

Additionally, 95% confidence intervals were calculated for each of these measures for each region.

The statistical findings and their interpretations are listed below for each of the three regions individually.

TABLE 3

Segment 1: Gain of chromosome 13

| Measure | Value | 95% Confidence Interval | |
|---|---|---|---|
| Relative Risk | 101.00 | 23.044 | 101.00 |
| Odds Ratio | Infinite | NA | NA |
| Sensitivity | 0.968 | 0.873 | 0.968 |
| Specificity | 1.00 | 0.970 | 1.00 |
| Misclassification Rate | 0.008 | 0.008 | 0.053 |

TABLE 4

Segment 2: Loss of chromosome 19

| Measure | Value | 95% Confidence Interval | |
|---|---|---|---|
| Relative Risk | 15.286 | 8.786 | 9.417 |
| Odds Ratio | Infinite | NA | NA |
| Sensitivity | 0.774 | 0.663 | 0.774 |
| Specificity | 1.00 | 0.966 | 1.00 |
| Misclassification Rate | 0.053 | 0.053 | 0.106 |

TABLE 5

Segment 3: Gain of chromosome 36

| Measure | Value | 95% Confidence Interval | |
|---|---|---|---|
| Relative Risk | 21.00 | 10.953 | 21.00 |
| Odds Ratio | Infinite | NA | NA |
| Sensitivity | 0.839 | 0.731 | 0.839 |
| Specificity | 1.00 | 0.966 | 1.00 |
| Misclassification Rate | 0.038 | 0.038 | 0.089 |

In all three cases, since aneuploidy of chromosomes 13, 19 and 36 were not detected in specimens from any of >100 'healthy' dogs, aneuploidy for each of the regions provides a high level of specificity (>99% in the current data set) that the dog from which the biopsy/urine sample was taken presented with neoplastic cells/TCC. Further, the physiology of the dog would suggest that any aberrant cells are highly likely to be derived from the bladder or urogenital tract and so the chances of the aberrant cancer not being of urogenital origin is very small. In consideration of the data presented, we may deduce that the combination of these aberrations is consistent with that expected from cells derived from a canine TCC.

6.5. Combinatorial Analysis.

To evaluate the potential predictive power of a multivariate model (using up to all three regions together, with gain and loss information for all three regions included), a decision tree model was constructed using the J48 algorithm. With or without cross-validation, the best tree only had a single variable included, copy number gain of CFA 13. This was the best model, adding the additional variables neither improved nor weakened the model.

In addition, if cells from a urinary tract present with two or more of the three aberrations above, the sensitivity and specify to indicate the presence of neoplasm is extremely high (>99%, based on the data set evaluated).

The detection of the two most frequent aneuploidies, gain of CFA 13/gain of CFA 36, renders an OR of 422.230, a RR of 33.817, and misclassification is 0. All confidence intervals are undefined.

The data described above provide the basis for the discovery that;

the detection of one or more of three major aberrations, defined as copy number gain of CFA 13, copy number loss of CFA 19, and copy number gain of CFA 36, whether in whole or part, in cellular specimens obtained from the urogenital tract of a dog, male or female, whether the specimen represents a biopsy of the suspect mass, or urine, would indicate the presence of abnormal cells, where such cells could be described as neoplastic and also as likely derived from a transitional cell carcinoma of the urogenital tract.

Any method that is able to detect and quantify the copy number status of CFA 13 and/or, CFA 19 and/or CFA 36, either in part or in entirety, may be used to enable this invention. Such approaches may include, but are not restricted to, (1) conventional cytogenetic assessment of metaphase preparations obtained from canine patient samples, (2) fluorescence in situ hybridization (FISH) whereby one or more probes representing part or all of CFA 13 and/or 19 and/or 36 are brought into contact with cells derived from canine patients, be they cells from a mass or from a urine sample of the patient. Such probes may, though are not restricted to, those representing the full or partial length of the chromosomes being detected and quantified (e.g., whole or partial chromosome paint probes), probes classified as 'locus specific' and which bind to a specific regions of the chromosome being assessed, and which have been determined suitable for the detection and quantification of that region. Single locus probes may comprise one or more fragments of single stranded or double stranded nucleic acid, in some forms as cloned fragments propagated in a bacterial of bacteriophage host (e.g., BAC, PAC, phage, cosmid, plasmid and others) and in other forms generated by PCR amplification of the specific sequences reported in the genome sequence. In these case the probes may be labeled with a hapten and subject to detection with a suitable chromogen or fluorophore post hybridization, using procedures widely known to those skilled in the art, or may themselves be labeled with a fluorophore prior to the hybridization so that they may report the site of hybridization immediately following hybridization and suitable washing steps known widely to those skilled in the art. In an alternate form the probe may comprise collections of numerous single or double stranded nucleic acid sequences (e.g. oligonucleotides that may be of varying length), where the sequences are designed based on available nucleic acid sequences representing the regions to be detected and enumerated, which may be labeled with a fluorophore. For example, but not limited to, such probes may be designed to detect the regions defined by the grey vertical lines in FIG. 1, representing the peak of the aberration frequencies in the cohort of TCC cases assessed, recognizing that any of these precise locations may move as additional cases are evaluated.

(3) polymerase chain reaction (PCR) using DNA isolated from patient samples; amplification based methods are used widely to obtained relative and absolute copy number of nuclei acid in a specimen, be that, for example, conventional PCR, quantitative PCR (qPCR) or droplet digital PCR (ddPCR). For example, in the design of a qPCR or ddPCR assay, the determination of the absolute concentration of amplicons based on the TCC samples evaluated would require the amplification of sequences that reside on CFA 13, 19 and 36, optionally in the regions representing the peaks of each aberration. For example, the vertical grey lines in FIGS. 1A and 1C represent selected ~1 Mb intervals demonstrating example peaks of aberration for CFA 13, 19 and 36 (indicated by FASST2 analysis of log 2 rations) and a region of CFA 8 that was copy number neutral when assessed by FASST2 analysis of log 2 ratio data. Each of the above base locations are derived from the boundaries of copy number events and derived from canfam2 (UCSC genome browser) and could be relocated into the current version of canine genome assembly (CanFam3), publicly available at ENSEMBLE and USCS. Use of a nucleic sequence within, but not restricted to this small region of CFA 8 may thus be used to establish a neutral copy number status in TCC when using qPCR and ddPCR, from which the relative concentration of amplicons (and thus copy number) may be deduced for regions assessed for copy number aberration, in this example, but not limited to the defined basepair locations noted on CFA 13, 19 and 36.

(4) comparative genomic hybridization. Any format of array that can provide an indication of copy number of a 'test' specimen may be used. Many methods for using immobilized nucleic acids on a range of solid surfaces are widely known to those skilled in the art.

(5) Next generation sequencing methods can determine that the abundance of the target regions as being greater than or less than expected based on the abundance of regions known to be normal.

Example 1

To provide an example of how one of the above approaches may be used in practice, a four color cytogenetic assay was developed using canine bacterial artificial chromosome (BAC) clones designed to hybridize to each of these chromosomes. Canine BAC clones (Table 5) were selected from the CHORI-82 canine library to provide a means to detect and quantify dog chromosomes 13, 19 and 36 by fluorescence in situ hybridization (FISH) of cells obtained from canines. A fourth FISH probe was developed to represent a region of dog chromosome 8 that was observed to be copy number neutral in all 31 cases of TCC biopsies evaluated.

TABLE 6

Identification of four canine BAC clones from the CHORI-82 canine BAC library that were used to provide a means to detect and quantify the copy number of CFA 8, CFA 13, CFA 19 and CFA 36 when used in multicolor FISH analysis of individual cells obtained from patient samples with confirmed TCC. All four BACs are selected from the set cytogenetically verified in house and reported previously [4].

| Target chromosome | CHORI-82 clone | Chromosome location (bp) (canfam2) | Probe size (bp) | Label color |
|---|---|---|---|---|
| CFA 8 | CH82-122f23 | 7984903-8129058 | 144156 | gold |
| CFA 13 | CH82-328p06 | 8630922-8818498 | 187577 | red |
| CFA 19 | CH82-122m01 | 25119452-25264995 | 145543 | green |
| CFA 36 | CH82-122f03 | 23199386-23269766 | 70380 | Pink (cy5) |

Four color FISH was performed on cells isolated from free-catch urine samples obtained from healthy dogs and from dogs with a confirmed diagnosis of TCC. DNA was prepared from the BAC clones identified in Table 6 and labeled to incorporate one of four spectrally resolvable fluorochrome conjugate dNTPs, each using standard protocols and which we have published previously e.g. [4, 5]. The four probes were mixed and hybridized to cells isolated from urine obtained from healthy and cancer bearing dogs, using protocols used widely in the art and which we have published previously e.g. [4, 5]. The inclusion of unlabeled dog DNA representing repetitive elements dispersed throughout the genome was included to suppress hybridization of any repetitive element within the four BAC probes to genomic sites other than their primary unique location in the canine genome. Images were acquired using a multicolor FISH workstation equipment with narrow pass fluorescence filters for wavelengths representing light seen in color as gold, red, green and Cy5 (far red) and a cooled CCD camera. Cell nuclei were counterstained in DAPI. Each color plane was imaged as black and white and then the fluorescence signal detected for each plane was pseudo-colored to recapitulate the color associated with the wavelengths passing through each filter (Cy5 signal is far red and so was presented as a pink)

FIG. 2 illustrates the hybridization characteristics of all four probes when contacted with the chromosome of a non-neoplastic cell, demonstrating that, under the conditions used (standard for those in the art), each of the four probes detects two copies of the specific and unique region of the canine genome, localized at the designated physical location of the appropriate pair of homologous chromosomes.

FIG. 2. Multicolor Hybridization of Fluorescence In Situ Hybridization Probes Designed to Detect and Quantify Dog Chromosomes 8, 13, 19 and 36.

Figure 2A:
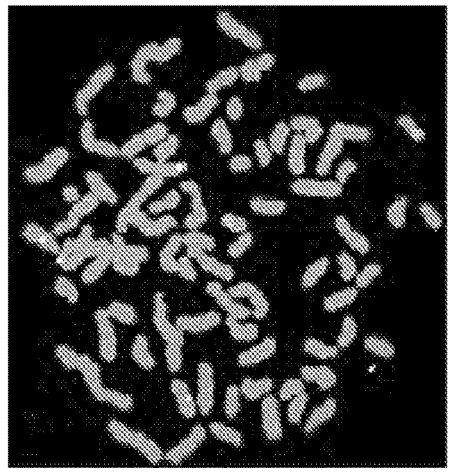
FIG. 2 shows multicolor FISH hybridization using probes designed to detect and quantify dog chromosomes 8, 13, 19 and 36.
Figure 2B:
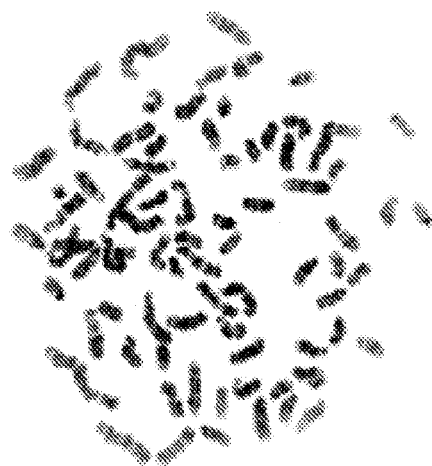
Figure 2C:
Figure 2C:
Figure 2C:
Figure 2C:

In cases of canine urogenital carcinoma/TCC, dog chromosome (CFA) 13 and 36 are subject to copy number increase (n>2), while CFA 19 is subject to copy number decrease (n<2). In the same cells CFA 8 has a balanced copy number (n=2). In this example canine BAC clones were selected to represent CFA 8, 13, 19 and 36 at the Mb locations in panel C. DNA from the four BAC clones was labeled for use in fluorescence in situ hybridization (FISH) analysis using the incorporation of four spectrally resolvable fluorophores enabling detection as separate sites of hybridization; CFA8=gold, CFA13=red, CFA 19=green, CFA 36=pink (shown as gray scale). FIG. 2A shows the four FISH probes hybridized to a dog metaphase preparation from a cell obtained from healthy dog, where the dog chromosomes are counterstained in DAPI, resulting in a blue color. FIG. 2B is the same image as panel A, processed to reveal the DAPI banding in gray scale. FIGS. 2A and 2B demonstrate that each probe hybridizes to just two regions of the genome, with each site representing the homologues of chromosomes 8, 13, 19 and 36. FIG. 2C shows one of each pair of homologues from panel B now enlarged and correctly oriented to demonstrate the chromosomal location of the hybridization signal. Beside each chromosome is shown the chromosome number and the precise physical location on that chromosome (in Mb) to which the selected probe binds.

Figure 3:
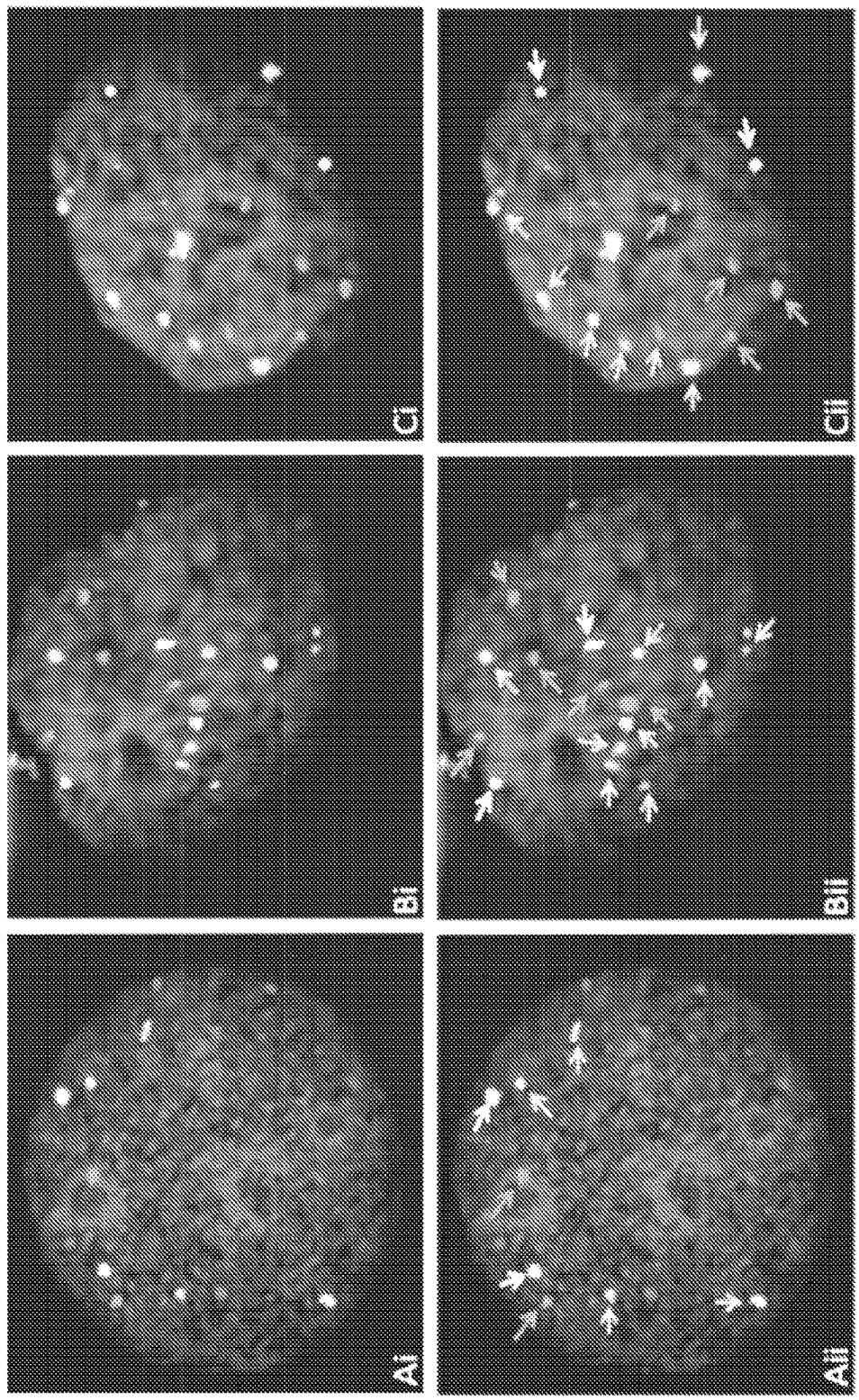
FIG. 3 shows multicolor FISH hybridization using probes designed to detect and quantify dog chromosomes 8, 13, 19 and 36. Panel (A) is a healthy dog and panels (B) and (C) are confirmed cases of TCC.

FIG. 3 illustrates the typical pattern of hybridization of the same four probes when hybridized to a non-neoplastic cell from a urine specimen of a healthy dog and to cells obtained from free catch urine obtained from dogs with confirmed transitional cell carcinoma. In healthy cells the copy number of all four probes is n=2. In the two cells shown to represent examples of those obtained from TCC bearing dogs, while the copy number of the probe representing CFA 8 is n=2, the copy number of the probe representing CFA 19 is n=1 and the copy number of the probes representing CFA 13 and CFA 16 are both n>2.

FIG. 3. Examples of using multicolor (five-plane) FISH analysis to detect and quantify probes representing CFA 8 (gold), 13 (red), 19 (green) and 36 (pink) in DAPI (blue counterstain) (shown as gray scale) cells obtained from urine samples of A) a healthy dog and B&C) two dogs with a confirmed diagnosis of a transitional cell carcinoma of the bladder. In Ai/Bi/Ci the five-color plane image is shown and in Aii/Bii/Cii the same five-color plane is presented with the sites of hybridization each arrowed with the corresponding color.

In Panel A/Ai it is evident that all four probes are present as two distinct copies (n=2), indicative of a 'healthy/copy number balanced' status. In B/Bi and C/Ci both cells have a balanced copy number of the CFA 8 probe (n=2), as expected, while each has just one copy of the probe representing CFA 8 (green) and multiple copies of the probes representing CFA 13 (red) and CFA 36 (pink) (shown as gray scale). The large size of some of the hybridization sites for the probes representing CFA 13 (red) and CFA 36 (pink) is indicative of tandem duplications at the sites of hybridization and so determination of the precise copy number per cell, over the actual number of visible sites of hybridization, is not possible. We may therefore state that in cells B and C the copy number of the probes representing CFA 13 are n>5 and n>4, respectively, and that in cells B and C the copy number of the probe representing CFA 36 is n>7 and n>6, respectively. In these two cells both have aneuploidy of all three target regions.

The example shown above may be used to represent a 'kit' suitable for detecting and evaluating the target chromosomes in canine cells. To evaluate the frequency of aneuploidy of the three target chromosomes within cells shed from the urogenital tract of dogs diagnosed with TCC, we evaluated up to 30 cells in each of 10 urine samples. Across all 10 cases the frequency of cells with aberrant copy mean number of cells for each of the three target regions and the number range in frequencies of aberration are show in Table 6. These data demonstrate that among the cases evaluated the minimum number of cells aberrant for at least one of the three regions was 23%.

TABLE 7

Summary of proportions of cells exhibiting copy number aberrations of CFA 13, CFA 19 and CFA 36 in populations of cells obtained from urine samples of dogs with a confirmed diagnosis of TCC.

| Aberration | Frequency of aberrant cells per case | Mean % of aberrant cells per case |
|---|---|---|
| +CFA 13 | 55%-100% | 88% |
| −CFA 19 | 23%-80% | 41% |
| +CFA 36 | 35%-100% | 84% |

Further, in eight of the ten cases evaluated, 100% of the cells had one or more of the three target aberrations, while the remaining two cases had 93% and 87% of cells with one or more of the target aberrations. These data provide sufficient evidence to allow the implementation of a diagnostic FISH based assay to confirm the presence of abnormal cells, highly suggestive of a TCC, by detection and quantification of the three chromosomes above, based on enumeration of cells shed from the urogenital tract into the urine.

Example 2

To provide an example of how this invention may be used in the form of a quantitative PCR assay, the invention was also reduced to practice in the form of a droplet digital PCR (ddPCR) assay. The peaks of copy number aberration for CFA 13, 19 and 36 were defined as shown by the grey vertical lines in FIG. 1; representing a ~1 Mb regions of CFA 13 at chr13:35-36 Mb, CFA 19 at chr19:25-26 Mb and CFA 36 at chr36:23-24 Mb using canfam2. In addition, the copy number neutral region of CFA8, located at chr8:7-8 Mb was included to represent a region of the genome unchanged in copy number in canine TCC.

The DNA sequence of the canine genome within each of the three defined regions of aberration on CFA 13, 19 and 36, and the 'neutral' region on CFA 8, were evaluated and used to design four TaqMan® MGB assays suitable for use in DNA copy number analysis The details of each of the four assays are presented in Table 8. In this example the BioRad QX100 droplet digital PCR system was used to determine copy number of the three target assays (located on CFA 13, 19 and 36) relative to that of the 'copy number neutral assay located on CFA 8.

Table 8. DNA sequences (from canfam2) and genome locations of each PCR primer and TaqMan probes used in the four paired assays developed to detect and quantify copy number of specific regions of CFA 13, 19 and 36 in cases of canine TCC. For each copy number assay one of the three test assays is mixed with the reference assay and the PCR run as a duplex reaction. The assay shows were developed to work with equal performance using the same PCR cycling conditions. Probes, primer and amplicons are SEQ ID NOS: 1-16.

TABLE 8

| TCC ddPCR assays | label | primer/probe sequence (5'-3') | | start base | end base |
|---|---|---|---|---|---|
| Reference assay | | | | | |
| CFA 8 | n/a | forward primer SEQ ID NO: 1 | CCAGGATTCTGCAGAGTTTGAT | CFA8:7695383 | CFA8:7695404 |
| | HEX | TaqMan probe SEQ ID NO: 2 | AATGCCTTTGACCAGTGGGTAGCC | CFA8:7695347 | CFA8:7695370 |
| | n/a | reverse primer SEQ ID NO: 3 | GTGGTGGAGGATTTGGAAGAAG | CFA8:7695302 | CFA8:7695323 |
| | amplicon sequence | Ccaggattctgcagagtttgatttgttgtttgaaaatgcc tttgaccagtgggtagccagcacagcctcagaaaaatgca ccttcttccaaatcctccaccac SEQ ID NO: 4 | | amplicon length | 103 bp |
| Test assay | | | | | |
| CFA 13 | n/a | forward primer SEQ ID NO: 5 | AGGACTATGTGTAAATCAGTAAGATAGG | CFA13:35393771 | CFA13:35393798 |
| | FAM | TaqMan probe SEQ ID NO: 6 | TGAATGAGGTTGAGGATGAAGCAAGGT | CFA13:35393822 | CFA13:35393848 |
| | n/a | reverse primer SEQ ID NO: 7 | CCCACTTCATGACCATATCCC | CFA13:35393854 | CFA13:35393874 |
| | amplicon sequence | Aggactatgtgtaaatcagtaagataggcctgtatagtatgaaga atggattgaatgaggttgaggatgaagcaaggttagttgggatat ggtcatgaagtggg SEQ ID NO: 8 | | amplicon length | 104 bp |
| CFA 19 | n/a | forward primer SEQ ID NO: 9 | GGACTGCTGAACTTCCTTCAT | CFA19:25520681 | CFA19:25520701 |
| | FAM | TaqMan probe SEQ ID NO: 10 | AGGTCCAATATTGCAATGAGTGAAGCA | CFA19:25520739 | CFA19:25520765 |
| | n/a | reverse primer SEQ ID NO: 11 | CTGTGGCTTCCTCATCGTTT | CFA19:25520768 | CFA19:25520787 |
| | amplicon sequence | ggactgctgaacttccttcatttctcagtcatcagcaaactaaga gaagtaaactttaagGtccaatattgcaatgagtgaagcataaaa cgatgaggaagccacag SEQ ID NO: 12 | | amplicon length | 107 bp |

TABLE 8-continued

| TCC ddPCR assays | label | | primer/probe sequence (5'-3') | start base | end base |
|---|---|---|---|---|---|
| CFA 36 | n/a | forward primer SEQ ID NO: 13 | TGCATGTCAAGAGAGGAGAATG | CFA36:23654179 | CFA36:23654200 |
| | FAM | TaqMan probe SEQ ID NO: 14 | CCACTTGCTCATATGTACACCTGATTGTCC | CFA36:23654229 | CFA36:23654258 |
| | n/a | reverse primer SEQ ID NO: 15 | TCCAGCTTGCAGAGTTGTT | CFA36:23654260 | CFA36:23654279 |
| | amplicon sequence | | Tgcatgtcaagagaggagaatgtgagaattttaattgctctaaataa agaccacttgctcatatgtacacctgattgtccaaaacaactctgca agctgga SEQ ID NO: 16 | amplicon length | 101 bp |

Each TaqMan assay was designed to provide an amplicon of 100-110 bp, with each amplified using the same thermal cycling conditions. DNA was isolated from the same urine samples used to provide material for FISH analysis shown as example 1, so that data generated by FISH and ddPCR were of the same cases. The 'reference' assay (CFA 8) was labeled with HEX and the three 'test' assays (CFA 13, 19 and 36) were each labeled with FAM. Each copy number assessment was processed as a pair of TaqMan assays in a single tube/well, comprising the reference assay and one of the three test assays. For each duplex/paired reaction, reaction components (i.e. sample DNA, PCR master mix, forward and reverse primers, HEX labeled TaqMan probe for the reference region on CFA 8 and FAM labeled TaqMan probe for the test region on either of CFA 13 or 19 or 36), were mixed into a single tube/well. The QX100 droplet generator was the used to partition each sample into up to 20,000 one nanoliter-sized droplets. Following thermal cycling of the reagents within each droplet, using protocols known well to those in the art, droplets from each sample were streamed in single file in the QX100 droplet reader and the number of positive and negative droplets for each of the test and reference amplicons was detected. The amplicon/PCR-positive and amplicon/PCR-negative droplets were counted to provide absolute quantification in digital form. When the concentration/microliter of each of the three test assays were normalized to the concentration/microliter of the reference assay in the same tube/well, the a mean copy number of the 'test' region in the DNA sample was determined. Data for all three paired assays are shown in FIG. 4, indicating that ddPCR is able to accurately detect and quantify the copy number status of aberrant regions, providing an alternate means to FISH based assessment for identification of aberrant DNA samples.

Figure 4:
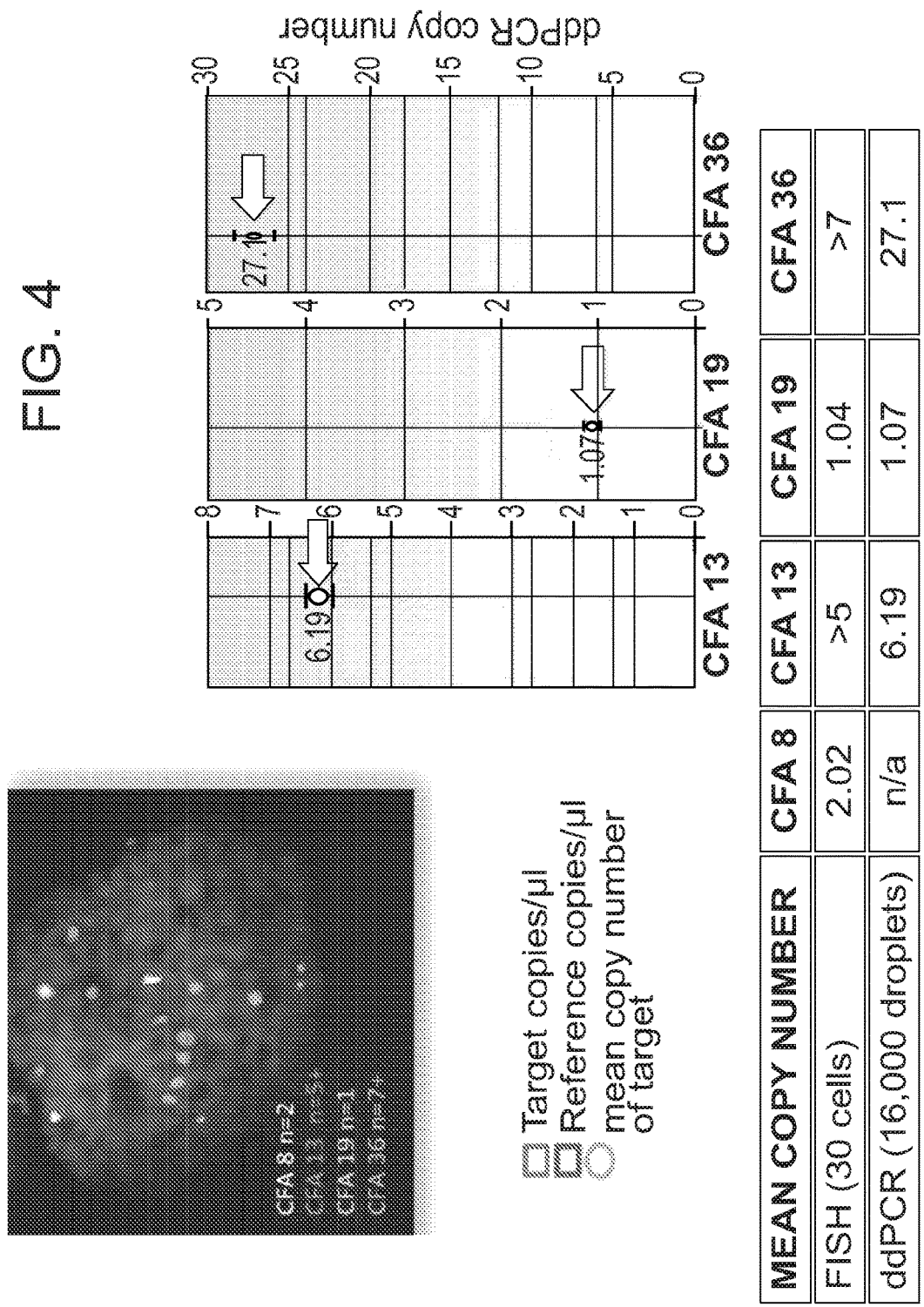
FIG. 4 shows the results of both FISH copy number analysis and an alternative embodiment, PCR method, to measure copy number.

FIG. 4. Example of the use of ddPCR to determine the mean DNA copy number of aberrant regions of the canine genome in DNA samples obtained from urine specimens of TCC bearing dogs. The inset FISH image is the same cell as shown in FIG. 3, panel B, where the copy number of the single locus probes for CFA 8, 13, 19 and 36 were recorded as n=2, n=>5, n=1 and n=>7. When 30 cells from that TCC patient were analyzed, the mean copy number of each of the probes remained constant. ddPCR data for the three aberrant regions are shown in the main body of the figure. The chart for each region is presented with three data points, the concentration of the target sequence/amplicon (i.e., of CFA 13 or 19 or 36), the concentration of the reference sequence/amplicon (i.e. CFA 8), and the derived mean copy number of the target sequence/amplicon (arrowed) obtained by normalization to the concentration of the reference sequence/amplicon (CFA 8). A summary of the mean copy number for each of the four regions (CFA 8, 13, 19 and 36), by assessment of 30 individual cells using the FISH approach reported in example 1, is presented in the table. The mean DNA copy number for the 'test' regions (CFA 13, 19 and 36) relative to the 'reference region (CFA 8). Resulting from an assessment of 16,000 1 nl droplet PCR reactions, is also shown.

The ddPCR derived mean copy number of the regions on CFA 13, CFA 19 and CFA 36 were n=6.19, n=1.07 and n=27.1. The value for the mean copy number of the region on CFA 19 (n=1.07) is comparable to the mean value obtained by analysis of 30 individual cells (n=1.02). For CFA 13 and CFA 36, the FISH data indicated that the mean copy number was n>5 and n>7, respectively, while the ddPCR data for these two regions indicate mean copy numbers of n=6.19 and n=27.1, respectively. These data support the basis of using a ddPCR based assay to accurately detect and quantify copy number of target regions, providing added value to FISH analysis for enumeration of regions where the additional copies are tandemly duplicated and thus non-resolvable by FISH.

7. REFERENCES

1. Mutsaers, A. J., W. R. Widmer, and D. W. Knapp, *Canine transitional cell carcinoma.* J Vet Intern Med, 2003. 17(2): p. 136-44.
2. Thomas, R., et al., *Refining tumor-associated aneuploidy through 'genomic recoding' of recurrent DNA copy number aberrations in* 150 *canine non-Hodgkin lymphomas.* Leukemia & lymphoma, 2011. 52(7): p. 1321-35.
3. Seiser, E. L., et al., *Reading between the lines: molecular characterization of five widely used canine lymphoid tumour cell lines.* Veterinary and comparative oncology, 2011.
4. Thomas, R., et al., *A genome assembly-integrated dog* 1 *Mb BAC microarray: a cytogenetic resource for canine cancer studies and comparative genomic analysis.* Cytogenet Genome Res, 2008. 122(2): p. 110-21.
5. Breen, M., et al., *An integrated* 4249 *marker FISH/RH map of the canine genome.* BMC Genomics, 2004. 5(1): p. 65.

It is to be understood that, while the invention has been described in conjunction with the detailed description, thereof, the foregoing description is intended to illustrate and not limit the scope of the invention. Other aspects, advantages, and modifications of the invention are within the scope of the claims set forth below. All publications, patents, and patent applications cited in this specification are herein incorporated by reference as if each individual publication or patent application were specifically and individually indicated to be incorporated by reference.

What is claimed is:

1. A method for diagnosing and treating a urogenital malignancy in a dog, the method comprising:
   (a) measuring a copy number of CFA 13, CFA 19, CFA 36, or any combination thereof in a biological sample from a dog; wherein:
      (i) the biological sample is selected from the group consisting of a urine sample, cells isolated from the urinary tract of the dog, and a combination thereof; and
      (ii) the copy number of CFA 13, 19, and/or 36 is measured by aberrations at CFA chr13:35-36 Mb, CFA chr13:8630922-8818498, CFA chr19:25-26 Mb, and/or CFA chr36:23-24 Mb using canfam2;
   (b) detecting an elevated copy number of CFA 13 and/or CFA 36 compared to a normal control or a reduced copy number of CFA 19 compared to a normal control;
   (c) diagnosing a urogenital malignancy in the dog; and
   (d) treating the urogenital malignancy in the dog with surgery, radiation therapy, chemotherapy, or any combination thereof.

2. The method of claim 1, wherein the copy number of CFA 13, CFA 19 and CFA 36 are measured.

3. The method of claim 1, wherein the copy number(s) is measured by fluorescence in situ hybridization (FISH).

4. The method of claim 1, wherein the copy number(s) is measured by polymerase chain reaction (PCR).

5. The method of claim 1, wherein the copy number(s) is measured by comparative genomic hybridization (CCH).

6. The method of claim 1, wherein the copy number(s) is measured by next generation sequencing.

7. The method of claim 1, wherein the biological sample is a urine sample.

8. The method of claim 1, wherein the sample is a fresh-frozen sample.

9. The method of claim 1, wherein the sample is a fresh sample.

10. The method of claim 1, wherein the sample is a formalin-fixed, paraffin-embedded sample.

11. The method of claim 1, wherein aberrations at CFA chr13:8630922-8818498, CFA chr19:25119452-25264995, and CFA chr36:23199386-23269766 are measured.

12. A method for selecting and treating a dog for a urogenital malignancy, the method comprising:
   (a) measuring a copy number of CFA chr13:35-36 Mb, CFA chr13:8630922-8818498, CFA chr19:25-26 Mb, and/or CFA chr36:23-24 Mb in a biological sample from a dog, wherein the biological sample is selected from the group consisting of a urine sample, cells isolated from the urinary tract of the dog, or a combination thereof isolated from the dog using canfam2;
   (b) detecting an elevated copy number of CFA chr13:35-36 Mb, CFA chr13:8630922-8818498, and/or CFA chr36:23-24 Mb compared to a normal control or a reduced copy number of CFA chr19:25-26 Mb compared to a normal control;
   (c) diagnosing a urogenital malignancy in the dog; and
   (d) selecting and treating the dog for the urogenital malignancy, wherein the treating comprises surgery, radiation therapy, chemotherapy, or any combination thereof.

13. The method of claim 12, wherein the copy numbers of CFA chr13:35-36 Mb, CFA chr19:25-26 Mb, and CFA chr36:23-24 Mb are measured.

14. The method of claim 12, wherein the sample is a fresh-frozen sample.

15. The method of claim 12, wherein the sample is a fresh sample.

16. The method of claim 12, wherein the sample is a formalin-fixed, paraffin-embedded sample.

17. The method of claim 12, wherein aberrations at CFA chr13:8630922-8818498, CFA chr19:25119452-25264995, and CFA chr36:23199386-23269766 are measured.

* * * * *